(12) United States Patent
Eger et al.

(10) Patent No.: US 11,367,512 B2
(45) Date of Patent: *Jun. 21, 2022

(54) METHODS AND SYSTEMS FOR DATA ANALYSIS

(71) Applicant: eResearchTechnology, Inc., Pittsburgh, PA (US)

(72) Inventors: Jason Eger, Pittsburgh, PA (US); Jon McClelland, Morgan Hill, CA (US); Dave Peterson, Scotts Valley, CA (US)

(73) Assignee: eResearchTechnology, Inc., Philadelphia, PA (US)

(*) Notice: Subject to any disclaimer, the term of this patent is extended or adjusted under 35 U.S.C. 154(b) by 282 days.

This patent is subject to a terminal disclaimer.

(21) Appl. No.: 16/294,296

(22) Filed: Mar. 6, 2019

(65) Prior Publication Data

US 2020/0043356 A1 Feb. 6, 2020

Related U.S. Application Data

(63) Continuation of application No. 13/688,962, filed on Nov. 29, 2012, now Pat. No. 10,276,054.

(60) Provisional application No. 61/564,654, filed on Nov. 29, 2011.

(51) Int. Cl.
*G09B 7/00* (2006.01)
*G16H 10/20* (2018.01)
*G06Q 30/02* (2012.01)

(52) U.S. Cl.
CPC ............. *G16H 10/20* (2018.01); *G06Q 30/02* (2013.01); *G09B 7/00* (2013.01)

(58) Field of Classification Search
CPC ... G09B 7/00; G09B 5/00; G09B 9/00; G16H 10/20; G06Q 30/02; G06Q 30/0203; G06Q 30/0204; G06Q 30/0202
See application file for complete search history.

(56) References Cited

U.S. PATENT DOCUMENTS

| D247,251 S | 2/1978 | Napoli |
| 4,262,632 A | 4/1981 | Hanton et al. |
| 4,343,375 A | 8/1982 | Manning |
| 4,353,375 A | 10/1982 | Colburn et al. |
| 4,367,752 A | 1/1983 | Jimenez et al. |
| 4,543,955 A | 10/1985 | Schroeppel |

(Continued)

FOREIGN PATENT DOCUMENTS

| EP | 0299667 A1 | 1/1989 |
| EP | 1034734 A1 | 9/2000 |

(Continued)

OTHER PUBLICATIONS

Alwan, et al. A Smart and Passive Floor-Vibration Based Fall Detector for Elderly. Information and Communication Technologies, 2006. ICTTA '06. 2nd vol. 1, Apr. 24-28, 2006 pp. 1003-1007.

(Continued)

*Primary Examiner* — Robert J Utama
(74) *Attorney, Agent, or Firm* — Wilson Sonsini Goodrich & Rosati

(57) ABSTRACT

Provided herein are systems, methods, and computer readable medium for entering, identifying, and aggregating data for analysis data in an electronic device, wherein the data are from a plurality of multi-participant surveys.

31 Claims, 6 Drawing Sheets

(56) References Cited

U.S. PATENT DOCUMENTS

| | | | |
|---|---|---|---|
| 4,566,461 | A | 1/1986 | Lubell et al. |
| 4,592,018 | A | 5/1986 | Wiegman |
| 4,686,624 | A | 8/1987 | Blum et al. |
| 4,803,625 | A | 2/1989 | Fu et al. |
| 4,841,986 | A | 6/1989 | Marchbanks |
| 4,844,076 | A | 7/1989 | Lesho et al. |
| 4,883,063 | A | 11/1989 | Bernard et al. |
| 4,909,260 | A | 3/1990 | Salem et al. |
| 4,918,627 | A | 4/1990 | Garcia et al. |
| 4,966,154 | A | 10/1990 | Cooper et al. |
| 4,974,601 | A | 12/1990 | Tranjan et al. |
| 4,975,842 | A | 12/1990 | Darrow et al. |
| 4,987,897 | A | 1/1991 | Funke |
| 5,002,064 | A | 3/1991 | Allain et al. |
| 5,063,937 | A | 11/1991 | Ezenwa et al. |
| 5,078,134 | A | 1/1992 | Heilman et al. |
| 5,111,818 | A | 5/1992 | Suzuki et al. |
| 5,113,859 | A | 5/1992 | Funke |
| 5,128,552 | A | 7/1992 | Fang |
| 5,131,390 | A | 7/1992 | Sakaguchi et al. |
| 5,137,345 | A | 8/1992 | Waldorf et al. |
| 5,181,519 | A | 1/1993 | Bible |
| 5,197,489 | A | 3/1993 | Conlan |
| 5,199,439 | A | 4/1993 | Zimmerman et al. |
| 5,213,106 | A | 5/1993 | Lerner |
| 5,213,555 | A | 5/1993 | Hood et al. |
| 5,218,969 | A | 6/1993 | Bredesen et al. |
| 5,222,503 | A | 6/1993 | Ives et al. |
| 5,226,424 | A | 7/1993 | Bible |
| 5,226,539 | A | 7/1993 | Cheng |
| 5,228,450 | A | 7/1993 | Sellers |
| 5,243,998 | A | 9/1993 | Silverman et al. |
| 5,253,654 | A | 10/1993 | Thomas et al. |
| 5,261,412 | A | 11/1993 | Butterfield et al. |
| 5,271,405 | A | 12/1993 | Boyer et al. |
| 5,275,159 | A | 1/1994 | Griebel |
| 5,280,429 | A | 1/1994 | Withers |
| 5,289,824 | A | 3/1994 | Mills et al. |
| 5,307,262 | A | 4/1994 | Ertel |
| 5,307,263 | A | 4/1994 | Brown |
| 5,412,769 | A | 5/1995 | Maruoka et al. |
| 5,447,164 | A | 9/1995 | Shaya et al. |
| 5,454,376 | A | 10/1995 | Stephens |
| 5,479,339 | A | 12/1995 | Miller |
| 5,547,878 | A | 8/1996 | Kell |
| 5,560,368 | A | 10/1996 | Berger |
| 5,583,831 | A | 12/1996 | Churchill et al. |
| 5,596,994 | A | 1/1997 | Bro |
| 5,652,146 | A | 7/1997 | Kell |
| 5,671,734 | A | 9/1997 | Pugh |
| 5,672,154 | A | 9/1997 | Sillen et al. |
| 5,704,366 | A | 1/1998 | Tacklind et al. |
| 5,710,551 | A | 1/1998 | Ridgeway |
| 5,732,709 | A | 3/1998 | Tacklind et al. |
| 5,778,882 | A | 7/1998 | Raymond et al. |
| 5,809,997 | A | 9/1998 | Wolf |
| 5,832,448 | A | 11/1998 | Brown |
| 5,898,586 | A | 4/1999 | Jeatran et al. |
| 5,908,788 | A | 6/1999 | Kell |
| 5,960,403 | A | 9/1999 | Brown |
| 5,963,136 | A | 10/1999 | O'Brien |
| 5,980,429 | A | 11/1999 | Nashner |
| 6,029,144 | A | 2/2000 | Barrett et al. |
| 6,039,688 | A | 3/2000 | Douglas et al. |
| 6,050,951 | A | 4/2000 | Friedman et al. |
| 6,051,029 | A | 4/2000 | Paterson et al. |
| 6,063,028 | A | 5/2000 | Luciano |
| 6,075,755 | A | 6/2000 | Zarchan |
| 6,095,985 | A | 8/2000 | Raymond et al. |
| 6,108,635 | A | 8/2000 | Herren et al. |
| 6,138,008 | A | 10/2000 | Dunn et al. |
| 6,151,581 | A | 11/2000 | Kraftson et al. |
| 6,151,586 | A | 11/2000 | Brown |
| 6,165,142 | A | 12/2000 | Bar |
| 6,167,362 | A | 12/2000 | Brown et al. |
| 6,171,237 | B1 | 1/2001 | Avitall et al. |
| 6,282,441 | B1 | 8/2001 | Raymond et al. |
| 6,302,844 | B1 | 10/2001 | Walker et al. |
| 6,317,731 | B1 | 11/2001 | Luciano |
| 6,338,039 | B1 | 1/2002 | Lonski et al. |
| 6,370,423 | B1 | 4/2002 | Guerrero et al. |
| 6,381,577 | B1 | 4/2002 | Brown |
| 6,440,069 | B1 | 8/2002 | Raymond et al. |
| 6,514,200 | B1 | 2/2003 | Khouri |
| 6,640,134 | B2 | 10/2003 | Raymond et al. |
| 6,663,846 | B1 | 12/2003 | McCombs et al. |
| 6,687,190 | B2 | 2/2004 | Momich et al. |
| 6,827,670 | B1 | 12/2004 | Stark et al. |
| 6,847,840 | B2 | 1/2005 | Depasquale et al. |
| 6,865,519 | B2 | 3/2005 | Lampert et al. |
| 6,879,970 | B2 | 4/2005 | Shiffman et al. |
| 6,895,405 | B1 | 5/2005 | Choi et al. |
| 6,980,958 | B1 | 12/2005 | Surwit et al. |
| 6,996,560 | B1 | 2/2006 | Choi et al. |
| 7,010,683 | B2 | 3/2006 | Corella |
| 7,011,939 | B2 | 3/2006 | Trumbull et al. |
| 7,054,782 | B2 | 5/2006 | Hartlaub |
| 7,058,517 | B1 | 6/2006 | Denton et al. |
| 7,072,802 | B2 | 7/2006 | Hartlaub |
| 7,124,059 | B2 | 10/2006 | Wetzer et al. |
| 7,185,065 | B1 | 2/2007 | Holtzman et al. |
| 7,249,043 | B1 | 7/2007 | Trout, II et al. |
| 7,251,609 | B1 | 7/2007 | McAlindon et al. |
| 7,251,620 | B2 | 7/2007 | Walker et al. |
| 7,273,454 | B2 | 9/2007 | Raymond et al. |
| 7,311,666 | B2 | 12/2007 | Stupp et al. |
| 7,343,337 | B1 | 3/2008 | Cieliebak et al. |
| 7,415,447 | B2 | 8/2008 | Shiffman et al. |
| 7,725,816 | B2 | 5/2010 | Cottrille et al. |
| 7,752,059 | B2 | 7/2010 | Sweeney |
| 7,783,072 | B2 | 8/2010 | Work et al. |
| 7,840,393 | B1 | 11/2010 | Whirley et al. |
| 7,873,589 | B2 | 1/2011 | Shiffman et al. |
| 8,065,180 | B2 | 11/2011 | Hufford et al. |
| 8,065,347 | B1 | 11/2011 | Demeyer et al. |
| 8,145,519 | B2 | 3/2012 | Hufford et al. |
| 8,209,002 | B2 | 6/2012 | Vajdic et al. |
| 8,273,019 | B2 | 9/2012 | Crowley et al. |
| 8,311,618 | B2 | 11/2012 | Vajdic et al. |
| 8,380,531 | B2 | 2/2013 | Paty et al. |
| 8,433,605 | B2 | 4/2013 | Hufford et al. |
| 8,533,029 | B2 | 9/2013 | Hufford et al. |
| 9,075,900 | B2 | 7/2015 | Wilson et al. |
| 9,129,215 | B2 | 9/2015 | Shiffman et al. |
| 9,483,618 | B2 | 11/2016 | Brincat et al. |
| 9,881,062 | B2 | 1/2018 | Shiffman et al. |
| 9,977,583 | B2 | 5/2018 | Calderwood et al. |
| 10,025,910 | B2 | 7/2018 | Paty et al. |
| 10,049,368 | B2 | 8/2018 | Hansen et al. |
| 10,296,196 | B2 | 5/2019 | Calderwood et al. |
| 10,555,702 | B1 | 2/2020 | Couderc et al. |
| 10,610,115 | B1 | 4/2020 | Zapesochny et al. |
| 2001/0044408 | A1 | 11/2001 | Reitberg |
| 2002/0007303 | A1* | 1/2002 | Brookler ............ G06Q 30/0203 705/7.32 |
| 2002/0013516 | A1 | 1/2002 | Freyre et al. |
| 2002/0019748 | A1 | 2/2002 | Brown |
| 2002/0042726 | A1 | 4/2002 | Mayaud |
| 2002/0052858 | A1 | 5/2002 | Goldman et al. |
| 2002/0064095 | A1 | 5/2002 | Momich et al. |
| 2002/0082886 | A1 | 6/2002 | Manganaris et al. |
| 2002/0087704 | A1 | 7/2002 | Chesnais et al. |
| 2002/0099570 | A1 | 7/2002 | Knight |
| 2002/0120471 | A1 | 8/2002 | Drazen |
| 2002/0143563 | A1 | 10/2002 | Hufford et al. |
| 2002/0143577 | A1 | 10/2002 | Shiffman et al. |
| 2002/0143595 | A1 | 10/2002 | Frank et al. |
| 2002/0156640 | A1 | 10/2002 | Hufford et al. |
| 2003/0036683 | A1 | 2/2003 | Kehr et al. |
| 2003/0065669 | A1 | 4/2003 | Kahn et al. |
| 2003/0069751 | A1 | 4/2003 | Lichtenstein et al. |
| 2003/0144874 | A1 | 7/2003 | Barret et al. |
| 2003/0178031 | A1 | 9/2003 | Du et al. |
| 2003/0194704 | A1 | 10/2003 | Penn et al. |

(56) References Cited

U.S. PATENT DOCUMENTS

| | | | |
|---|---|---|---|
| 2003/0229533 A1* | 12/2003 | Mack | G06Q 30/02 705/7.32 |
| 2004/0024639 A1 | 2/2004 | Goldman | |
| 2004/0049418 A1* | 3/2004 | Watanabe | G06Q 30/0203 705/12 |
| 2004/0068690 A1* | 4/2004 | Wood | G06F 40/10 715/205 |
| 2004/0073476 A1* | 4/2004 | Donahue | G06Q 30/0203 705/7.32 |
| 2004/0078236 A1* | 4/2004 | Stoodley | G16H 10/60 705/2 |
| 2004/0122701 A1 | 6/2004 | Dahlin et al. | |
| 2004/0186750 A1 | 9/2004 | Surbey et al. | |
| 2004/0210472 A1* | 10/2004 | Lew | G06Q 30/0203 705/7.32 |
| 2004/0215402 A1 | 10/2004 | Hsiung et al. | |
| 2005/0004814 A1 | 1/2005 | Seltzer | |
| 2005/0038680 A1 | 2/2005 | McMahon | |
| 2005/0131739 A1 | 6/2005 | Rabinowitz et al. | |
| 2005/0154676 A1 | 7/2005 | Ronning et al. | |
| 2005/0159979 A1* | 7/2005 | Dickson | G16H 15/00 705/2 |
| 2005/0165626 A1 | 7/2005 | Karpf | |
| 2005/0229223 A1 | 10/2005 | Katagishi et al. | |
| 2006/0026054 A1* | 2/2006 | Barel | G06Q 30/0203 705/7.37 |
| 2006/0136267 A1 | 6/2006 | Brackett et al. | |
| 2006/0167346 A1 | 7/2006 | Sarel | |
| 2006/0174111 A1 | 8/2006 | Burns | |
| 2006/0184493 A1 | 8/2006 | Shiffman et al. | |
| 2007/0055481 A1 | 3/2007 | Baird et al. | |
| 2007/0106565 A1 | 5/2007 | Coelho | |
| 2007/0149214 A1 | 6/2007 | Walsh et al. | |
| 2007/0179361 A1 | 8/2007 | Brown et al. | |
| 2007/0238936 A1 | 10/2007 | Becker | |
| 2007/0250429 A1 | 10/2007 | Walser et al. | |
| 2008/0004904 A1 | 1/2008 | Tran | |
| 2008/0013701 A1 | 1/2008 | Barhydt et al. | |
| 2008/0013705 A1 | 1/2008 | Yoffie et al. | |
| 2008/0021741 A1 | 1/2008 | Holla et al. | |
| 2008/0052259 A1 | 2/2008 | Shiffman et al. | |
| 2008/0097908 A1 | 4/2008 | Dicks et al. | |
| 2008/0097910 A1 | 4/2008 | Dicks et al. | |
| 2008/0119705 A1 | 5/2008 | Patel et al. | |
| 2008/0154640 A1 | 6/2008 | Demeyer et al. | |
| 2008/0162229 A1 | 7/2008 | Moore | |
| 2008/0177574 A1 | 7/2008 | Lara Gonzalez et al. | |
| 2008/0228525 A1 | 9/2008 | Weickert et al. | |
| 2008/0320417 A1 | 12/2008 | Begley et al. | |
| 2009/0055220 A1 | 2/2009 | Rapaport et al. | |
| 2009/0281829 A1 | 11/2009 | Hansen et al. | |
| 2009/0318779 A1 | 12/2009 | Tran | |
| 2010/0010358 A1 | 1/2010 | Boute et al. | |
| 2010/0022847 A1 | 1/2010 | Crowley et al. | |
| 2010/0023346 A1 | 1/2010 | Paty et al. | |
| 2010/0029294 A1 | 2/2010 | Matsuoka | |
| 2010/0145730 A1 | 6/2010 | Abreu | |
| 2010/0174558 A1 | 7/2010 | Smith et al. | |
| 2010/0218132 A1 | 8/2010 | Soni et al. | |
| 2010/0228699 A1 | 9/2010 | Webber et al. | |
| 2010/0279718 A1 | 11/2010 | Borve | |
| 2011/0108623 A1 | 5/2011 | Hammad | |
| 2011/0119155 A1 | 5/2011 | Hammad et al. | |
| 2011/0152656 A1 | 6/2011 | Weinert et al. | |
| 2011/0153360 A1 | 6/2011 | Hanina et al. | |
| 2011/0161111 A1 | 6/2011 | Dicks et al. | |
| 2011/0172550 A1 | 7/2011 | Martin et al. | |
| 2011/0202368 A1 | 8/2011 | Stakutis et al. | |
| 2011/0208529 A1 | 8/2011 | Jeal et al. | |
| 2011/0213225 A1 | 9/2011 | Bernstein et al. | |
| 2011/0251469 A1 | 10/2011 | Varadan | |
| 2012/0010518 A1 | 1/2012 | Sarel | |
| 2012/0018506 A1 | 1/2012 | Hammad et al. | |
| 2012/0029940 A1 | 2/2012 | Hufford et al. | |
| 2012/0041767 A1 | 2/2012 | Hoffman et al. | |
| 2012/0041786 A1 | 2/2012 | Yu | |
| 2012/0084210 A1 | 4/2012 | Farahmand | |
| 2012/0232929 A1 | 9/2012 | Experton | |
| 2012/0239414 A1 | 9/2012 | Hufford et al. | |
| 2012/0253847 A1 | 10/2012 | Dell'Anno et al. | |
| 2013/0006671 A1 | 1/2013 | Hufford et al. | |
| 2013/0157244 A1 | 6/2013 | Eger et al. | |
| 2013/0159010 A1 | 6/2013 | Paty et al. | |
| 2013/0159021 A1 | 6/2013 | Felsher | |
| 2013/0268287 A1 | 10/2013 | Hufford et al. | |
| 2014/0108032 A1 | 4/2014 | Hufford et al. | |
| 2015/0178473 A1 | 6/2015 | Hufford et al. | |
| 2015/0178474 A1 | 6/2015 | Hufford et al. | |
| 2016/0034541 A1 | 2/2016 | Shiffman et al. | |
| 2016/0045117 A1 | 2/2016 | Liu et al. | |
| 2016/0284058 A1 | 9/2016 | Calderwood et al. | |
| 2017/0273597 A1 | 9/2017 | Schuelke et al. | |
| 2017/0337043 A1 | 11/2017 | Brincat et al. | |
| 2018/0150523 A1 | 5/2018 | Shiffman et al. | |
| 2018/0300049 A1 | 10/2018 | Calderwood et al. | |
| 2018/0374560 A1 | 12/2018 | Paty et al. | |
| 2019/0043060 A1 | 2/2019 | Hansen et al. | |

FOREIGN PATENT DOCUMENTS

| | | |
|---|---|---|
| FR | 2686497 A1 | 7/1993 |
| WO | WO-8802237 A1 | 4/1988 |
| WO | WO-8905116 A1 | 6/1989 |
| WO | WO-9401040 A1 | 1/1994 |
| WO | WO-9401049 A1 | 1/1994 |
| WO | WO-9413198 A1 | 6/1994 |
| WO | WO-9424929 A1 | 11/1994 |
| WO | WO-9613790 A1 | 5/1996 |
| WO | WO-9625877 A2 | 8/1996 |
| WO | WO-9838909 A1 | 9/1998 |
| WO | WO-9927483 A1 | 6/1999 |
| WO | WO-9938052 A1 | 7/1999 |
| WO | WO-0015103 A1 | 3/2000 |
| WO | WO-0069331 A1 | 11/2000 |
| WO | WO-0075748 A2 | 12/2000 |
| WO | WO-0106433 A1 | 1/2001 |
| WO | WO-0109701 A1 | 2/2001 |
| WO | WO-0126020 A1 | 4/2001 |
| WO | WO-0126021 A1 | 4/2001 |
| WO | WO-0134024 A1 | 5/2001 |
| WO | WO-0174229 A2 | 10/2001 |
| WO | WO-0178345 A1 | 10/2001 |
| WO | WO-0219247 A2 | 3/2002 |
| WO | WO-0219247 A3 | 11/2003 |
| WO | WO-2006009331 A1 | 1/2006 |
| WO | WO-2007056822 A1 | 5/2007 |
| WO | WO-2008001295 A2 | 1/2008 |
| WO | WO-2008001295 A3 | 2/2008 |
| WO | WO-2009017820 A2 | 2/2009 |
| WO | WO-2017165761 A1 | 9/2017 |

OTHER PUBLICATIONS

Appeal from the United States District Court for the Western District of Pennsylvania in Case No. 2:15-cv-00918-NBF, Judge Nora Barry Fischer. Appeal No. 16-2281. Judgment. Entered Mar. 17, 2017. 2 pages.

Appeal from the United States District Court for the Western District of Pennsylvania in Case No. 2:15-cv-00918-NBF, Judge Nora Barry Fischer. Filed Sep. 7, 2016. Appeal No. 16-2281. 174 pages.

Arzy, et al. Self in time: Imagined self-location influences neural activity related to mental time travel. The Journal of Neuroscience. Jun. 18, 2008; 28(25):6502-6507.

Bethel, et al. Mining for Implications in Medical Data. Conference Paper, 2006. 18th International Conference on Pattern Recognition (ICPR'06). pp. 1212-1215. 10.1109/ICPR.2006.800.

Bradburn, et al. Answering autobiographical questions: the impact of memory and inference on surveys. Science. Apr. 10, 1987;236(4798):157-61.

(56) References Cited

OTHER PUBLICATIONS

Chen, et al. Rule based clinical decision support system for hematological disorder. Conference Paper, May 2013. Proceedings of the IEEE International Conference on Software Engineering and Service Sciences, ICSESS. 43-48. 10.1109/ICSESS.2013.6615252.
Cole, et al. A comparative study of mobile electronic data entry systems for clinical trial data collection. International Journal of Medicinal Informactics. 2006; 75:722-729.
Collins, et al. Ecological momentary assessment in a behavioral drinking moderation training program. Exp. Clin. Psychopharmacol. Aug. 1998;6(3):306-315.
Coons, et al. Recommendations on evidence needed to support measurement equivalence between electronic and paper-based patient-reported outcome (PRO) measures: ISPOR ePRO Good Research Practices Task Force report. Value Health. Jun. 2009;12(4):419-29. Epub Nov. 11, 2008.
Co-pending U.S. Appl. No. 11/002,046, filed Jan. 12, 2014.
Co-pending U.S. Appl. No. 15/583,723, filed May 1, 2017.
Co-pending U.S. Appl. No. 15/604,368, filed May 24, 2017.
Co-pending U.S. Appl. No. 15/955,461, filed Apr. 17, 2018.
Co-pending U.S. Appl. No. 16/007,633, filed Jun. 13, 2018.
Co-pending U.S. Appl. No. 16/020,109, filed Jun. 27, 2018.
Cramer, et al. How often is medication taken as prescribed? JAMA Jun. 9, 1989;261(22):3273-3277.
Dahlstrom et al. Patient Computers to Enhance Compliance with Completing Questionnaires: a Challenge for the 1990s. Patient Compliance in Medical Practice and Clinical Trials (ed. By J.A. Cramer and B. Spilker). New York: Raven Press;1991: 233-40.
Dale, et al. Despite technical problems personal digital assistants outperform pen and paper when collecting patient diary data. Journal of Clinical Epidemiology. 2007; 60:8-17.
Deser, et al. Time travel? Extended version of the talk presented at '46 LNX 46, Cambridge, MA. 1992. p. 1-19.
Dillman, et al. Design effects in the transition to web-based surveys. Am J Prev Med. 2007; 32(5S):S90-96.
Eich, et al. Memory for pain: relation between past and present pain intensity. Pain. Dec. 1985;23(4):375-80.
Engfer, et al. Technology in service of science. Invivodata, Inc. Jan. 30, 2001 (9 pages).
eResearchTechnology GmbH. MasterScope ©: Diagnostic Platform for Centralized Spirometry, ECG and Home Monitoring. © 2014 eResearchTechnology GmbH. Rev. 02, May 30, 2014. 4 pages.
eResearchTechnology GmbH. SpiroPro © CT: Handheld Spirometer and Pulse Oximeter. © 2014 eResearchTechnology GmbH. Rev. 01, Jul. 2014. 2 pages.
ERT ©. ERT Introduces Updated Diagnostic Platform for Centralized Spirometry, ECG, and Home Monitoring in Respiratory Clinical Trials. Web article. Jun. 16, 2014. 4 pages. URL:<https://www.ert.com/ert-introduces-updated-diagnostic-platform-for-centralized-spirometry-ecg-and-home-monitoring-in-respiratory-clinical-trials/>.
FDA. Guidance for industry. Computerized systems used in clinical investigations. US department of health and human services. May 2007.
Friedman, et al. Memory for the time of past events. Psychological bulletin. 1993, vol. 113, No. 1, pp. 44-66.
Gorin, et al. Recall Biases and Cognitive Errors in Retrospective Self-Reports: A Call for Momentary Assessments. Handbook of Heath Psychology. Lawrence Erlbaum Assoc.:Mahwah, New Jersey. 2001;pp. 405-413.
Greeno, et al. Binge antecedents in obese women with and without binge eating disorder. J. Consult Clin. Psychol. Feb. 2000;68(1):95-102.
Guadadango, et al. Using PDAs for data collection. Applied Nursing Research. Nov. 2004; 17(4):283-291.
Gwaltney, et al. Equivalence of electronic and paper-and-pencil administration of patient-reported outcome measures: a meta-analytic review. Value Health. 2008; 11:322-333.
https://web.archive.org/web/20001201220000/http://www.crfbox.com. Accessed Sep. 28, 2015.
https://web.archive.org/web/20010201072400/http://crfbox.com. Accessed Sep. 28, 2015.
https://web.archive.org/web/20010226175201/http://crfbox.com. Accessed Sep. 28, 2015.
https://web.archive.org/web/20010402003750/http://crfbox.com. Accessed Sep. 28, 2015.
https://web.archive.org/web/20010710204214/http://www.crfbox.com/2.2.html. Accessed Oct. 5, 2015.
https://web.archive.org/web/20010710204327/http://www.crfbox.com/2.3.html. Accessed on Oct. 5, 2015.
https://web.archive.org/web/20010713065230/http://www.crfbox.com/3.2.html. Accessed Sep. 28, 2015.
https://web.archive.org/web/20010718111538/http://www.crfbox.com/3.1.html. Accessed Sep. 28, 2015.
https://web.archive.org/web/20010719174752/http://www.crfbox.com/3.html. Accessed Oct. 5, 2015.
https://web.archive.org/web/20010721054420/http://www.crfbox.com/5.2.html. Accessed Oct. 5, 2015.
https://web.archive.org/web/20010725181157/http://www.crfbox.com/news/news5.html. Accessed Sep. 28, 2015.
https://web.archive.org/web/20010726213424/http://www.crfbox.com/news/news6.html. Accessed Oct. 5, 2015.
https://web.archive.org/web/20010812073633/http://www.crfbox.com/4.1.html. Accessed Oct. 5, 2015.
https://web.archive.org/web/20010812074841/http://www.crfbox.com/4.2.html. Accessed Oct. 5, 2015.
https://web.archive.org/web/20010905193509/http://www.crfbox.com/news/news4.html. Accessed Sep. 28, 2015.
https://web.archive.org/web/20011124003540/http://www.crfbox.com/news/news3.html. Accessed Sep. 28, 2015.
https://web.archive.org/web/20011222025011/http://www.crfbox.com/news/news2.html. Accessed Sep. 28, 2015.
https://web.archive.org/web/20020616090851/http://www.crfbox.com/news/news1.html. Accessed Sep. 28, 2015.
Hufford, et al. Collecting reliable and valid real-time patient experience data. Drug Information Journal. 2001; 755-765.
Hufford, et al. Correspondence between paper and electronic visual analog scales among adult asthmatics. Invivodata. Nov. 9, 2001 (5 pgs).
Hufford, et al. Quality of life and patient experience research. Invivodata, Inc. Jan. 30, 2001 (10 pages).
Hyland, et al. Diary keeping in asthma: comparison of written and electronic methods. BMJ. Feb. 20, 1993;306(6876):487-9.
Invivodata Announcement dated Jun. 13, 2000.
Invivodata. Application brief pain. Apr. 10, 2001 (2 pages).
Invivodata company newsletter dated 4th quarter 2001.
Invivodata company press release dated Apr. 11, 2001: Invivodata leads way in clinical trial technology with wireless patient diary system.
Invivodata company press release dated Jun. 12, 2000: Invivodata delivers new version of patient compliance monitoring.
Invivodata company press release dated Jun. 12, 2000: Invivodata Inc. provides science-based system to measure patient experience.
Invivodata company press release dated Nov. 28, 2000: Invivodata is first to guarantee patient compliance in clinical studies.
Invivodata company press release dated Oct. 12, 2000: Invivodata and RxCCI announce new partnership to improve quality and timeliness of clinical trials.
Invivodata. Comparing electronic and paper diary data. Invivodata. Nov. 26, 2001.
Invivodata. Guaranteed patient compliance. Insight into patient behavior. Reduced study risks. Jul. 2001.
Invivodata, Inc. Insights. Third Issue. Jul. 2001.
Invivodata. Innovations in Clinical Trial Technologies. Schedule for Seminar. 2001.
Invivodata invoice dated Oct. 11, 2006.
Invivodata postcard mail item. 2001.
Invivodata. Prove it—your drug's performance beats the competition. Jul. 2001.
Jamison, et al. Electronic diaries for monitoring chronic pain: 1-year validation study. Pain. Apr. 2001;91(3):277-85.
Kamarck, et al. Effects of task strain, social conflict, and emotional activation on ambulatory cardiovascular activity: daily life conse-

(56) References Cited

OTHER PUBLICATIONS quences of recurring stress in a multiethnic adult sample. Health Psychol. Jan. 17, 1998;(1): 17-29.
Kamarck, et al. Emotional Support Moderates The Acute Pressor Effects Of Stress During Daily Life Abstracts of Papers for 1999 Annual Meeting: Paper Session: Cardiovascular Activity in Relation to Stress Psychology and Neurobiology. Psychosomatic Medicine 1999;61(1):112 (abstract).
Kamarck, et al. The Diary of Ambulatory Behavioral States: A new Approach to the Assessment of Psychosocial Influences on Ambulatory Cardiovascular Activity. Technology and Methods in Behavioral Medicine (D.S. Krantz and A. Baum, eds.) Lawrence Erlbaum Associates:Mahwah, New Jersey. 1998; Chapter 9:163-193.
Kamarck, et al. The effects of psychosocial influences on ambulatory blood pressure: contrasting different measurement and data analytic strategies. 37th Annual Meeting of the Society for Psychophysical Research, N. Falmouth, Massachusetts, USA, Oct. 15-19, 1997; Psychophysiology 1997;34 (Suppl. 1):S6-S7.
Kiuchi et al. A World Wide Web-based User Interface for a Data Management System for Use in Multi-institutional clinical trials—Development and Experimental Operation of an Automated Patient Registration and Random Allocation System. Controlled Clinical Trials. New York: Elseviar Sciences, Inc.;1996:(17)476-493.
Koop, et al. The use of handheld computers in clinical trials. Controlled Clinical Trials. 2002; 23:469-480.
Letter dated Aug. 1, 2014 from Andrew P. Nemiroff of Cozen to Louis Lieto of Wilson Sonsini Goodrich & Rosati regarding U.S. Pat. Nos. 8,065,180; 8,145,519 and 8,433,605.
Letter dated May 14, 2014 from Andrew P. Nemiroff of Cozen to Louis Lieto of Wilson Sonsini Goodrich & Rosati regarding U.S. Pat. Nos. 8,065,180; 8,145,519 and 8,433,605.
Letter dated Oct. 1, 2015 from Andrew P. Nemiroff of Law Office of Andrew P. Nemiroff, Esq. to Edward G. Poplawski of Wilson Sonsini Goodrich & Rosati regarding *eResearch Technology, Inc.* v. *CRF, Inc.* (15-918).
Lorence, et al. Incremental adoption of information security in health-care organizations: implications for document management. IEEE Trans Inf Technol Biomed. Jun. 2005;9(2):169-73.
Lussier et al. PureMD: a Computerize Patient Record Software for Direct Data Entry by Physicians: Using a Keyboardless Pen-Based Portable Computer. American Medical Informatics Association, McGraw Hill. 1992;261-264.
McKenzie, et al. Proving the ediary dividend. Appl Clin Trials. Jun. 1, 2004.
Memorandum opinion dated May 10, 2016 for *Eresearchtechnology, Inc.* v. *CRF, Inc.* Civil Action No. 15-918, Hor. Hora Barry Fischer in the United States District Court for the Western District of Pennsylvania.
Missinou, et al. Short report: Piloting paperless data entry for clinical research in Africa. Am. J. Top. Med. Hyg. 2005; 72(3):301-303.
Mitchel, et al. The impact of electronic data capture on clinical data management: perspectives from the present into the future. Technology in Clinical Research. Aug. 2008; 37-41.
Notice of allowance dated Apr. 13, 2015 for U.S. Appl. No. 12/965,719.
Notice of allowance dated May 19, 2011 for U.S. Appl. No. 09/825,533.
Notice of allowance dated Jun. 3, 2008 for U.S. Appl. No. 11/324,504.
Notice of Allowance dated Jun. 14, 2013 for U.S. Appl. No. 13/603,035.
Notice of Allowance dated Sep. 1, 2017 for U.S. Appl. No. 14/792,126.
Notice of allowance dated Sep. 14, 2010 for U.S. Appl. No. 11/844,632.
Notice of allowance dated Sep. 24, 2004 for U.S. Appl. No. 09/825,534.
Notice of allowance dated Oct. 24, 2012 for U.S. Appl. No. 12/509,318.
Notice of allowance dated Dec. 19, 2012 for U.S. Appl. No. 13/399,150.
Notice of allowance dated Dec. 30, 2011 for U.S. Appl. No. 13/211,133.
O'Connell, et al. Coping in real time: using Ecological Momentary Assessment techniques to assess coping with the urge to smoke. Res. Nurs. Health. Dec. 21, 1998;(6):487497.
O'Connell, et al. Overcoming the Urge to Smoke: The Strategies of Long-Term Abstainers and Later Relapsers. Psychology of Addictive Behavior 1991;5(1):1-8.
O'Connell, et al. Reversal theory and smoking: a state-based approach to ex-smokers' highly tempting situations. J. Consult. Clin. Psychol. Aug. 1990;58(4):489-494.
O'Connell, et al. Symptom beliefs and actual blood glucose in type II diabetes. Res. Nurs. Health. Jun. 13, 1990;(3): 145-151.
O'Connell, K Why rational people do irrational things. The theory of psychological reversals. J. Psychosoc. Nurs. Ment. Health Serv. Jan. 29, 1991;(1):11-14.
Office action dated Jan. 3, 1996 for U.S. Appl. No. 08/394,157.
Office action dated Jan. 4, 2012 for U.S. Appl. No. 12/177,540.
Office Action dated Jan. 5, 2016 for U.S. Appl. No. 12/434,244.
Office action dated Jan. 8, 2008 for U.S. Appl. No. 11/002,046.
Office Action dated Jan. 17, 2018 for U.S. Appl. No. 13/688,962.
Office Action dated Jan. 22, 2015 for U.S. Appl. No. 13/838,698.
Office action dated Jan. 25, 2016 for U.S. Appl. No. 14/792,126.
Office action dated Jan. 26, 2007 for U.S. Appl. No. 09/840,730.
Office Action dated Jan. 26, 2017 for U.S. Appl. No. 12/434,244.
Office action dated Jan. 29, 2009 for U.S. Appl. No. 09/840,730.
Office Action dated Jan. 31, 2011 for U.S. Appl. No. 12/434,244.
Office action dated Feb. 7, 2006 for U.S. Appl. No. 10/693,232.
Office Action dated Feb. 8, 2016 for U.S. Appl. No. 13/838,698.
Office Action dated Feb. 8, 2017 for U.S. Appl. No. 14/670,261.
Office action dated Feb. 9, 2006 for U.S. Appl. No. 09/825,533.
Office action dated Feb. 10, 1997 for U.S. Appl. No. 08/394,157.
Office action dated Feb. 19, 2010 for U.S. Appl. No. 11/844,632.
Office action dated Feb. 20, 2015 for U.S. Appl. No. 13/688,962.
Office action dated Mar. 9, 2012 for U.S. Appl. No. 12/509,318.
Office action dated Mar. 12, 2013 for U.S. Appl. No. 13/603,035.
Office action dated Mar. 13, 2012 for U.S. Appl. No. 12/965,719.
Office action dated Mar. 20, 2015 for U.S. Appl. No. 13/670,151.
Office Action dated Mar. 24, 2014 for U.S. Appl. No. 12/434,244.
Office action dated Apr. 3, 2009 for U.S. Appl. No. 09/825,533.
Office Action dated Apr. 4, 2017 for U.S. Appl. No. 14/792,126.
Office action dated Apr. 11, 2007 for U.S. Appl. No. 10/693,232.
Office action dated Apr. 19, 2006 for U.S. Appl. No. 11/002,046.
Office action dated Apr. 21, 2016 for U.S. Appl. No. 13/670,151.
Office action dated Apr. 29, 2010 for U.S. Appl. No. 09/825,533.
Office action dated May 2, 2000 for U.S. Appl. No. 09/447,986.
Office Action dated May 5, 2017 for U.S. Appl. No. 14/579,670.
Office action dated May 8, 2014 for U.S. Appl. No. 12/965,719.
Office action dated May 18, 1999 for U.S. Appl. No. 09/001,032.
Office action dated May 20, 2008 for U.S. Appl. No. 09/825,533.
Office action dated May 20, 2016 for U.S. Appl. No. 13/801,853.
Office Action dated May 22, 2017 for U.S. Appl. No. 13/670,151.
Office action dated May 26, 2015 for U.S. Appl. No. 13/801,853.
Office action dated Jun. 7, 2011 for U.S. Appl. No. 12/177,540.
Office action dated Jun. 8, 2000 for U.S. Appl. No. 09/447,986.
Office Action dated Jun. 8, 2017 for U.S. Appl. No. 13/688,962.
Office Action dated Jun. 15, 2011 for U.S. Appl. No. 12/434,244.
Office action dated Jun. 16, 2008 for U.S. Appl. No. 09/840,730.
Office action dated Jun. 18, 2007 for U.S. Appl. No. 11/002,046.
Office Action dated Jun. 24, 2015 for U.S. Appl. No. 13/838,698.
Office action dated Jun. 26, 2014 for U.S. Appl. No. 13/801,853.
Office action dated Jun. 28, 2017 for U.S. Appl. No. 13/801,853.
Office action dated Jul. 2, 2014 for U.S. Appl. No. 13/670,151.
Office action dated Jul. 10, 1997 for U.S. Appl. No. 08/394,157.
Office action dated Jul. 12, 2005 for U.S. Appl. No. 11/002,046.
Office action dated Jul. 15, 2002 for U.S. Appl. No. 09/940,129.
Office action dated Jul. 17, 2007 for U.S. Appl. No. 09/840,730.
Office action dated Jul. 19, 2006 for U.S. Appl. No. 10/693,232.
Office Action dated Jul. 21, 2015 for U.S. Appl. No. 12/434,244.
Office Action dated Jul. 28, 2016 for U.S. Appl. No. 12/434,244.
Office action dated Aug. 31, 2016 for U.S. Appl. No. 13/670,151.

(56) References Cited

OTHER PUBLICATIONS

Office action dated Sep. 3, 2015 for U.S. Appl. No. 13/688,962.
Office Action dated Sep. 5, 2017 for U.S. Appl. No. 14/579,574.
Office action dated Sep. 8, 2006 for U.S. Appl. No. 09/825,533.
Office Action dated Sep. 8, 2017 for U.S. Appl. No. 14/670,261.
Office action dated Sep. 18, 2013 for U.S. Appl. No. 13/801,853.
Office Action dated Sep. 28, 2016 for U.S. Appl. No. 14/792,126.
Office action dated Sep. 29, 1998 for U.S. Appl. No. 09/001,032.
Office action dated Oct. 4, 2005 for U.S. Appl. No. 09/840,730.
Office action dated Oct. 4, 2011 for U.S. Appl. No. 12/965,719.
Office action dated Oct. 9, 2015 for U.S. Appl. No. 13/801,853.
Office action dated Oct. 11, 2012 for U.S. Appl. No. 12/965,719.
Office Action dated Oct. 13, 2016 for U.S. Appl. No. 14/579,670.
Office action dated Oct. 22, 2014 for U.S. Appl. No. 13/801,853.
Office action dated Nov. 14, 2007 for U.S. Appl. No. 11/324,504.
Office Action dated Nov. 16, 2016 for U.S. Appl. No. 13/688,962.
Office action dated Nov. 17, 2014 for U.S. Appl. No. 13/953,503.
Office action dated Nov. 22, 2013 for U.S. Appl. No. 13/801,853.
Office action dated Nov. 25, 2011 for U.S. Appl. No. 12/509,318.
Office action dated Nov. 26, 2010 for U.S. Appl. No. 09/825,533.
Office Action dated Nov. 29, 2017 for U.S. Appl. No. 14/579,670.
Office Action dated Dec. 1, 2014 for U.S. Appl. No. 12/434,244.
Office action dated Dec. 5, 2006 for U.S. Appl. No. 11/002,046.
Office action dated Dec. 19, 2002 for U.S. Appl. No. 09/940,129.
Office action dated Dec. 20, 2007 for U.S. Appl. No. 09/840,730.
Office action dated Dec. 30, 2010 for U.S. Appl. No. 12/177,540.
Palermo, et al. A randomized trial of electronic versus paper pain diaries in children: impact on complianc, accuracy, and acceptability. Pain. 2004; 107:213-219.
Palmblad, et al. Electronic diaries and questionnaires: designing user interfaces that are easy for all patients to use. Qual Life Res. Sep. 2004;13(7):1199-207.
Park, et al. 3B-1 Noninvasive Insulin Delivery in Large Pigs (> 100 lbs) Using the Lightweight Cymbal Array. Ultrasonics Symposium, 2007. IEEE Oct. 28-31, 2007 pp. 104-107 Digital Object Identifier 10.1109/ULTSYM.2007.39.
Paty, et al. The importance of assessing base rates for clinical studies: an example of stimulus control of smoking. The Experience of Psychopathology: Investigating Mental Disorders in their Natural Settings (DeVries, Marten W. ed.) Cambridge University Press:Cambride, England. 1992; pp. 347-352.
Penner, et al. Individual Differences in Intraperson Variability in Mood. Journal of Personality and Social Psychology 1994;66(4):712-721.
Potocky, et al. State-outcome consistency in smoking relapse crises: a reversal theory approach. J. Consult. Clin. Psychol. Apr. 1991;59(2):351-353.
Powell, J. Handhelds aid doctors. Retrieved from the Internet, www.bostonherald.com/business/technology/ palm07032000.htm. Jul. 3, 2000.
Prokscha. Electronic data capture systems. Practical Guide to Clinical Data Management, Second Edition. 2006; Ch 17:153-161.
Raymond, et al. Electronic Subject Diaries in Clinical Trials. Applied Clinical Trials. Mar. 2000; 8 pages.
Raynor, et al. The effects of social influence on cardiovascular responsiveness in the natural environment. 37th Annual Meeting of the Society for Psychophysical Research, N. Falmouth, Massachusetts, USA, Oct. 15-19, 1997,. Psychophysiology 1997;34 (Suppl. 1):S73.
Rekimoto, J. Time-machine computing: a time-centric approach for the information environment. UIST '99 Proceedings of the 12th annual ACM symposium on User interface software and technology. ACM New York, NY, USA © 1999; 45-54. CHI Letters vol. 1, 1.
Ross, et al. Relation of implicit theories to the construction of personal histories. Psychological review. 1989, vol. 96, No. 2, pp. 341-357.
Salford Systems. CART® for Windows User's Guide. A Salford Systems Implementation of the Original CART Program. 1999;i-v, 1-90, Index.

Schwartz, et al. Does trait coping exist? A momentary assessment approach to the evaluation of traits. J. Pers. Soc. Psychol. Aug. 1999;77(2):360-369.
Schwartz, et al. Strategies for analyzing ecological momentary assessment data. Health Psychol. Jan. 1998;17(1):6-16.
Shalev, et al. Towards an expert system for treatment planning. Engineering in Medicine and Biology Society, 1988. Proceedings of the Annual International Conference of the IEEE Nov. 4-7, 1988 pp. 1444-1445, vol. 3 Digital Object Identifier 10.1109/IEMBS.1988. 95302.
Sharma, et al. Multi-sensor Visual Analytics Supported by Machine-Learning Models. Conference Paper, Nov. 2015. IEEE International Conference on Data Mining Workshop (ICDMW), pp. 668-674. 10.1109/ICDMW.2015.190.
Shiffman, et al. A day at a time: predicting smoking lapse from daily urge. J. Abnorm. Psychol. Feb. 1997;106(1):104-116.
Shiffman, et al. Comparative efficacy of 24-hour and 16-hour transdermal nicotine patches for relief of morning craving. Addiction Aug. 2000;95(8): 1185-1195.
Shiffman, et al. Drinking and Smoking: A Field Study of their Association. Annals of Behavioral Medicine 1994;16(3):203-209.
Shiffman, et al. Dynamic effects of self-efficacy on smoking lapse and relapse Health Psychol. Jul. 2000;19(4):315-323.
Shiffman, et al. First lapses to smoking: within-subjects analysis of real-time reports. J. Consult. Clin. Psychol. Apr. 1996;64(2):366-379.
Shiffman, et al. Individual differences in the context of smoking lapse episodes. Addict. Behav. Nov.-Dec. 1997;22(6):797-811.
Shiffman, et al. Introduction to the special section: Ecological momentary assessment in health psychology. Health Psychology. Jan. 1988; 17(1):3-5.
Shiffman, et al. Methods of measuring patient experience: Paper versus electronic patient diaries. Invivodata, Inc. Jan. 30, 2001 (9 pages).
Shiffman, et al. Nicotine withdrawal in chippers and regular smokers: subjective and cognitive effects. Health Psychol. Jul. 1995;14(4):301-309.
Shiffman, et al. Patient experience: A growing focus in clinical trials. Invivodata, Inc. Jan. 30, 2001 (8 pages).
Shiffman, et al. Progression from a smoking lapse to relapse: prediction from abstinence violation effects, nicotine dependence, and lapse characteristics. J. Consult. Clin. Psychol. Oct. 1996;64(5):993-1002.
Shiffman, et al. Remember that? A comparison of real-time versus retrospective recall of smoking lapses. J. Consult. Clin. Psychol. Apr. 1997;65(2):292-300.
Shiffman, et al. Subject experience diaries in clinical research, Part 1: The patient experience movement; Part 2: Ecological momentary assessment. Applied Clinical Trials. Feb. & Mar. 2001 (12 pages).
Shiffman, et al. Temptations to smoke after quitting: a comparison of lapsers and maintainers. Health Psychol. Nov. 1996;15(6):455-461.
Shiffman, et al. The Abstinence Violation Effect Following Smoking Lapses and Temptations. Cognitive Therapy and Research 1997;21(5):497-523.
Shiffman, et al. The effect of bupropion on nicotine craving and withdrawal. Psychopharmacology Jan. 2000;148(1):33-40.
Shiffman, et al. The scientific principles underlying patient experience research: Ecological momentary assessment. Invivodata, Inc. Jan. 30, 2001 (8 pages).
Shiffman, S. Assessing Smoking Patterns and Motives. Journal of Consulting and Clinical Psychology 1993;61(5):732-742.
Shiffman, S. Real-Time Self-Report of Momentary States in the Natural Environment: Computerized Ecological Momentary Assessment. The Science of Self-Report: Implicates for Research and Practice (A. Stone, et al. eds.) Lawrence Erlbaum Associates:Mahwah, New Jersey. 1989; Chapter 16: 277-296.
Shingo, et al. Correlation of airway obstruction and patient-reported endpoints in clinical studies. Eur Respir J. Feb. 2001;17(2):220-4.
Smith, G. Statistical Reasoning 3rd edition. Needham Heights: Allyn and Bacon; 1991:619-67.

(56) References Cited

OTHER PUBLICATIONS

Stokes, et al. Developing and implementing electronic patient diaries: the clinical protocal. Applied Clinical Trials. 2003; 12(3):46-56.
Stokes, et al. Developing and Validating Electronic Diaries. Applied Clinical Trials. 2003; 68-78.
Stolworthy, et al. PDAs in clinical data management. SoCRA Source. Aug. 2003; 24-26.
Stone, et al. A comparison of coping assessed by ecological momentary assessment and retrospective recall. J. Pers. Soc. Psychol. Jun. 1998;74(6):1670-1680.
Stone, et al. Does the peak-end phenomenon observed in laboratory pain studies apply to real-world pain in rheumatoid arthritics? The Journal of Pain. Fall 2000;1(3):212-217.
Stone, et al. Ecological Momentary Assessment (EMA) in Behavioral Medicine. Annals of Behavioral Medicine 1994; 16(3): 199-202.
Stone, et al. Ecological Momentary Assessment. Well-being: The foundations of Hedonic psychology. Kahneman, Daniel et al. (eds.). Russell Sage Foundation: New York, NY. 1999;pp. 26-39.
Stone, et al. Patient non-compliance with paper diaries. BMJ. 2002; 324:1193-1194.
Straka, et al. Patient and self-reporting of compliance does not correspond with electronic monitoring: an evaluation using isosorbide dinitrate as a model drug. Pharmacotherapy. Jan.-Feb. 1997;17(1):126-132.
Straka, et al. Patient self-reporting of compliance does not correspond with electronic monitoring: an evaluation using isosorbide dinitrate as a model drug. Pharmacotherapy. Jan.-Feb. 1997;17(1):126-32.
Tattersall et al. The Use of a Hand-held Computer to Record Clinical Trial Data in General Practice: a Pilot Study. The Journal of International Medical Research. 1989;17:185-89.
Taylor et al. The use of a real-time computer diary for data acquisition and processing. Behav. Res. Ther.1990;(28)1:93-97.
The Gantry Group, LLC. ROI Value Driver Study for PalmTM Mobile Solutions: Clinical Trials. May 2003; 17 pages.
Tomkies, K. Taking a New Tack on Clinical Trial Data Collection: New Internet-based software aims to improve data integrity, helping speed data transmission in the process. Retrieved from the Internet www.office.com/global/0,,53-17789,FF.html. May 18, 2000.
Totterdell et al. In situ repeated measures of affect and cognitive performance facilitated by use of a hand-held computer. Behavior Research Methods, Instruments and Computers. 1992;24(4):545-53.
Tourangeau. Survey research and societal change. Annu Rev Psychol. 2004; 55:775-801.

U.S. Appl. No. 13/211,133, filed Aug. 16, 2011.
U.S. Appl. No. 13/399,150, filed Feb. 17, 2012.
U.S. Appl. No. 13/603,035, filed Sep. 4, 2012.
U.S. Appl. No. 13/801,853, filed Mar. 13, 2013.
U.S. Appl. No. 13/953,503, filed Jul. 29, 2013.
U.S. Appl. No. 14/579,574, filed Dec. 22, 2014.
U.S. Appl. No. 14/579,670, filed Dec. 22, 2014.
U.S. Appl. No. 14/792,126, filed Jul. 6, 2015.
U.S. Department of Health and Human Services FDA Center for Drug Evaluation and Research, et al. Guidance for industry: patient-reported outcome measures: use in medical product development to support labeling claims: draft guidance. Health Qual Life Outcomes. Oct. 11, 2006;4:79. 20 pages.
U.S. Department of Health and Human Services Food and Drug Administration, et al. Guidance for Industry Patient-Reported Outcome Measures: Use in Medical Product Development to Support Labeling Claims. Feb. 2006 Clinical/Medical.
U.S. Department of Health and Human Services Food and Drug Administration, et al. Guidance for Industry Patient-Reported Outcome Measures: Use in Medical Product Development to Support Labeling Claims. Feb. 2009 Clinical/Medical.
U.S. Appl. No. 12/434,244 Office Action dated Oct. 4, 2017.
U.S. Appl. No. 13/688,962 Office Action dated Apr. 13, 2018.
U.S. Appl. No. 14/579,574 Office Action dated Mar. 27, 2018.
U.S. Appl. No. 14/579,670 Office Action dated May 29, 2018.
U.S. Appl. No. 15/291,103 Office Action dated Oct. 5, 2018.
U.S. Appl. No. 15/955,461 Office Action dated Aug. 9, 2018.
Wang, et al. Molecular Diagnosis and Biomarker Identification on SELDI proteomics data by ADTBoost method. Conf Proc IEEE Eng Med Biol Soc. 2005;5:4771-4.
Weisspeiner, et al. Multichannel Ambulatory Monitoring of Circulation Related Biosignals. Proceedings. Computers in Cardiology, Sep. 23-26, 1991; Venice, Italy. IEEE Comput. Soc. Press: Los Alamitos, CA, USA. 1991;p. 457-460.
Wikipedia. Marketing research. Available at http://en.wikipedia.org/wiki/Marketing_research. Accessed Nov. 30, 2012.
Zimmet et al. Computer-Based Patient Monitoring Systems: Use in Research and Clinical Practice. Diabetes Care. Nov./Dec. 1988; (11) Supp. 1:62-6.
Zwiebel. EDC: A Brief Guide to Study Start-up. Published Aug. 2, 2002. http://www.appliedclinicaltrialsonline.com/appliedclinicaltrials/Feature+Article/EDC-A-Brief-Guide-to-Study-Start-up/ArticleStandard/Article/detail/83566. Accessed Sep. 10, 2012.
U.S. Appl. No. 15/583,723 Office Action dated Jun. 13, 2019.
U.S. Appl. No. 15/604,368 Office Action dated Feb. 26, 2019.
U.S. Appl. No. 16/007,633 Office Action dated Jun. 19, 2020.
U.S. Appl. No. 16/020,109 Office Action dated Dec. 30, 2019.

* cited by examiner

METHODS AND SYSTEMS FOR DATA ANALYSIS

CROSS REFERENCE

This application is a continuation application of U.S. application Ser. No. 13/688,962, filed Nov. 29, 2012, which claims the benefit of U.S. Provisional Patent Application No. 61/564,654, filed Nov. 29, 2011, which is herein incorporated by reference in its entirety.

BACKGROUND

There is a need for devices, apparatus, systems, and methods for collecting and recording information from a plurality of multi-participant surveys, e.g., clinical trials, on a single electronic device. Furthermore, there is a need for systems and methods for transmitting data from a plurality of multi-participant surveys stored on a single electronic device to a staging data repository, and then transmitting data from the staging data repository to selected study data repositories.

SUMMARY OF THE INVENTION

In one aspect, a method for managing data on an electronic device is provided, wherein the data are from a plurality of multi-participant surveys, wherein the data are managed for analysis, the method comprising: a) entering data from a first participant in a first multi-participant survey into the electronic device, wherein the data from the first participant are identified for analysis as being from the first participant or as being from the first multi-participant survey; b) entering data from a second participant in a second multi-participant survey into the electronic device, wherein the first multi-participant survey is different from the second multi-participant survey, and wherein the data from the second participant are identified for analysis as being from the second participant or as being from the second multi-participant survey; and c) aggregating the data from the first participant or the data from the first multi-participant survey for analysis, and aggregating the data from the second participant or the data from the second multi-participant survey for analysis.

In some embodiments, the data from the first participant comprise data from the first multi-participant survey, and the data from the second participant comprise data from the second multi-participant survey. In some embodiments, the method further comprises recording the data from the first participant in the first multi-participant survey and the data from the second participant in the second multi-participant survey on the electronic device. In some embodiments, the device is not a handheld electronic device. In some embodiments, the device is a workstation. In some embodiments, the electronic device is a handheld electronic device. In some embodiments, the handheld electronic device is a personal digital assistant, tablet computer, or a telephone. In some embodiments, the electronic device is connected to the Internet.

In some embodiments, the first multi-participant survey and the second multi-participant survey are concurrent. In some embodiments, the first multi-participant survey ends before the second multi-participant survey begins. In some embodiments, the first participant and the second participant are the same person. In some embodiments, the first participant and the second participant are different people. In some embodiments, the first participant enters the data from the first multi-participant survey into the electronic device, and the second participant enters the data from the second multi-participant survey into the electronic device. In some embodiments, a first individual enters the data from the first participant in the first multi-participant survey into the device, and a second individual enters the data from second participant in the second multi-participant survey into the device. In some embodiments, the first individual is a healthcare provider and the second individual is a healthcare provider. In some embodiments, the first individual and the second individual are the same healthcare provider. In some embodiments, the method further comprises entering data from at least 2, 3, 4, 5, 6, 7, 8, 9, 10, 50, 100, 1000, 10,000, 100,000, or 1,000,000 multi-participant surveys into the device.

In some embodiments, a plurality of participants participates in the first multi-participant survey and a plurality of participants participates in the second multi-participant survey. In some embodiments, the electronic device is in electronic communication with a staging data repository. In some embodiments, the staging data repository is a server. In some embodiments, the method further comprises transmitting the data identified as being from the first participant in the first multi-participant survey to the staging data repository and transmitting the data identified as being from the second participant in the second multi-participant survey to the staging data repository. In some embodiments, the method further comprises transmitting the data identified as being from the first multi-participant survey to the staging data repository and transmitting the data identified as being from the second multi-participant survey to the staging data repository.

In some embodiments, the staging data repository is in electronic communication with a plurality of study data repositories, wherein the plurality of study data repositories comprises a first study data repository and a second study data repository. In some embodiments, the method further comprises transferring, from the staging data repository, the data identified as being from the first participant in the first multi-participant survey to the first study data repository and the data identified as being from the second participant in the second multi-participant survey to the second study data repository. In some embodiments, the method further comprises transferring, from the staging data repository, the data identified as being from the first multi-participant survey to the first study data repository and the data identified as being from the second multi-participant survey to the second study data repository.

In some embodiments, the method further comprises locking at least one of the plurality of study data repositories. In another embodiment, the method further comprises adding a new study data repository to the plurality of study data repositories, wherein the new study data repository is in electronic communication with the staging data repository. In another embodiment, the plurality of study data repositories comprise at least 2, 3, 4, 5, 6, 7, 8, 9, 10, 50, 100, 1000, 10,000, 100,000, or 1,000,000 study data repositories.

In some embodiments, the plurality of multi-participant surveys is a plurality of clinical trials. In some embodiments, the plurality of multi-participant surveys is a plurality of market research surveys. In some embodiments, the plurality of multi-participant surveys is a plurality of political research surveys. In some embodiments, the method further comprises providing the electronic device to a site, wherein a plurality of participants communicates with the site. In some embodiments, the site is a hospital, medical clinic, or laboratory. In some embodiments, the plurality of participants communicates with the site through in-person visits. In some embodiments, the plurality of participants communicates with the site electronically. In some embodiments, the electronic communication comprises an e-mail, text, telephone call, or voice message.

In some embodiments, the method further comprises providing the electronic device to the first participant. In some embodiments, data identified as being from the first participant in the first multi-participant study are transferred from the staging data repository to the second study data repository, further comprising transferring, from the second study data repository to the first study data repository, the data identified as being from the first participant in the first multi-participant study that were transferred from the staging data repository to the second study data repository.

In another aspect, a computer readable medium having stored thereon sequences of instructions is provided which, when executed by a computer system, cause the computer system to perform: a) accepting data from a first participant in a first multi-participant survey in an electronic device, wherein the data from the first participant are identified for analysis as being from the first participant or as being from the first multi-participant survey; b) accepting data from a second participant in a second multi-participant survey in the electronic device, wherein the first multi-participant survey is different from the second multi-participant survey, and wherein the data from the second participant are identified for analysis as being from the second participant or as being from the second multi-participant survey; and c) aggregating the data from the first participant or the data from the first multi-participant survey for analysis, and aggregating the data from the second participant or the data from the second multi-participant survey for analysis.

In some embodiments, the data from the first participant comprise data from the first multi-participant survey, and the data from the second participant comprise data from the second multi-participant survey. In some embodiments, the computer system further performs recording the data from the first participant in the first multi-participant survey and the data from the second participant in the second multi-participant survey on the electronic device. In some embodiments, the device is not a handheld electronic device. In some embodiments, the device is a workstation. In some embodiments, the electronic device is a handheld electronic device. In some embodiments, the handheld electronic device is a personal digital assistant, tablet computer, or a telephone. In some embodiments, the electronic device is connected to the Internet.

In some embodiments, the first multi-participant survey and the second multi-participant survey are concurrent. In some embodiments, the first multi-participant survey ends before the second multi-participant survey begins. In some embodiments, the first participant and the second participant are the same person. In some embodiments, the first participant and the second participant are different people.

In some embodiments, the accepting the data from the first participant comprises accepting data input by the first participant, and the accepting the data from the second participant comprises accepting data input by the second participant. In some embodiments, the accepting the data from the first participant comprises accepting data input by a first individual, and accepting the data from the second participant comprises accepting data input by a second individual. In some embodiments, the first individual is a healthcare provider and the second individual is a healthcare provider. In some embodiments, the first individual and the second individual are the same healthcare provider.

In some embodiments, the computer readable medium has stored thereon sequences of instructions which, when executed by a computer system, cause the computer system to perform accepting data from at least 2, 3, 4, 5, 6, 7, 8, 9, 10, 50, 100, 1000, 10,000, 100,000, or 1,000,000 multi-participant surveys into the device. In some embodiments, a plurality of participants participates in the first multi-participant survey and a plurality of participants participates in the second multi-participant survey. In some embodiments, the electronic device is in electronic communication with a staging data repository. In some embodiments, the staging data repository is a server. In some embodiments, the computer readable medium has stored thereon sequences of instructions which, when executed by a computer system, cause the computer system to perform transmitting the data identified as being from the first participant in the first multi-participant survey to the staging data repository and transmitting the data identified as being from the second participant in the second multi-participant survey to the staging data repository. In some embodiments, the computer readable medium has stored thereon sequences of instructions which, when executed by a computer system, cause the computer system to perform transmitting the data identified as being from the first multi-participant survey to the staging data repository and transmitting the data identified as being from the second multi-participant survey to the staging data repository.

In some embodiments, the staging data repository is in electronic communication with a plurality of study data repositories, wherein the plurality of study data repositories comprises a first study data repository and a second study data repository. In some embodiments, the computer readable medium has stored thereon sequences of instructions which, when executed by a computer system, cause the computer system to perform transferring, from the staging data repository, the data identified as being from the first participant in the first multi-participant survey to the first study data repository and the data identified as being from the second participant in the second multi-participant survey to the second study data repository. In some embodiments, the computer readable medium has stored thereon sequences of instructions which, when executed by a computer system, cause the computer system to perform transferring, from the staging data repository, the data identified as being from the first multi-participant survey to the first study data repository and the data identified as being from the second multi-participant survey to the second study data repository.

In some embodiments, the computer readable medium has stored thereon sequences of instructions which, when executed by a computer system, cause the computer system to perform locking at least one of the plurality of study data repositories. In some embodiments, the plurality of study data repositories comprise at least 2, 3, 4, 5, 6, 7, 8, 9, 10, 50, 100, 1000, 10,000, 100,000, or 1,000,000 study data repositories.

In some embodiments, the plurality of multi-participant surveys is a plurality of clinical trials. In some embodiments, the plurality of multi-participant surveys is a plurality of market research surveys. In some embodiments, the plurality of multi-participant surveys is a plurality of political research surveys.

In some embodiments, the electronic device is located at a site. In some embodiments, the site is a hospital, medical clinic, or laboratory. In some embodiments, the electronic device accepts data from a plurality of participants that communicates with the site through in-person visits. In some embodiments, the electronic device accepts data from a plurality of participants that communicates with the site electronically. In some embodiments, the electronic communication comprises an e-mail, text, telephone call, or voice message.

In some embodiments, data identified as being from the first participant in the first multi-participant study is transferred from the staging data repository to the second study data repository, and the computer system further performs transferring, from the second study data repository to the first study data repository, the data identified as being from the first participant in the first multi-participant study that was transferred from the staging data repository to the second study data repository.

In another aspect, a system for managing data from a plurality of multi-participant surveys is provided, the system comprising computer readable instructions for: a) accepting data from a first participant in a first multi-participant survey in an electronic device, wherein the data from the first participant are identified for analysis as being from the first participant or as being from the first multi-participant survey; b) accepting data from a second participant in a second multi-participant survey in the electronic device, wherein the first multi-participant survey is different from the second multi-participant survey, and wherein the data from the second participant are identified for analysis as being from the second participant or as being from the second multi-participant survey; and c) aggregating the data from the first participant or the data from the first multi-participant survey for analysis, and aggregating the data from the second participant or the data from the second multi-participant survey for analysis.

In some embodiments, the data from the first participant comprise data from the first multi-participant survey, and the data from the second participant comprise data from the second multi-participant survey. In some embodiments, the system further comprises computer readable instructions for recording the data from the first participant in the first multi-participant survey and the data from the second participant in the second multi-participant survey on the electronic device.

In some embodiments, the device is not a handheld electronic device. In some embodiments, the device is a workstation. In some embodiments, the electronic device is a handheld electronic device. In some embodiments, the handheld electronic device is a personal digital assistant, tablet computer, or a telephone. In some embodiments, the electronic device is connected to the Internet.

In some embodiments, the first multi-participant survey and the second multi-participant survey are concurrent. In some embodiments, the first multi-participant survey ends before the second multi-participant survey begins. In some embodiments, the first participant and the second participant are the same person. In some embodiments, the first participant and the second participant are different people. In some embodiments, the accepting the data from the first participant comprises accepting data input by the first participant, and the accepting the data from the second participant comprises accepting data input by the second participant. In some embodiments, the accepting the data from the first participant comprises accepting data input by a first individual, and accepting the data from the second participant comprises accepting data input by a second individual. In some embodiments, the first individual is a healthcare provider and the second individual is a healthcare provider. In some embodiments, the first individual and the second individual are the same healthcare provider. In some embodiments, the system further comprises computer readable instructions for accepting data from at least 2, 3, 4, 5, 6, 7, 8, 9, 10, 50, 100, 1000, 10,000, 100,000, or 1,000,000 multi-participant surveys into the device. In some embodiments, a plurality of participants participates in the first multi-participant survey and a plurality of participants participates in the second multi-participant survey. In some embodiments, the electronic device is in electronic communication with a staging data repository. In some embodiments, the staging data repository is a server. In some embodiments, the system further comprises computer readable instructions for transmitting the data identified as being from the first participant in the first multi-participant survey to the staging data repository and transmitting the data identified as being from the second participant in the second multi-participant survey to the staging data repository.

In some embodiments, the system further comprises computer readable instructions for transmitting the data identified as being from the first multi-participant survey to the staging data repository and transmitting the data identified as being from the second multi-participant survey to the staging data repository. In some embodiments, the staging data repository is in electronic communication with a plurality of study data repositories, wherein the plurality of study data repositories comprises a first study data repository and a second study data repository.

In some embodiments, the system further comprises computer readable instructions for transferring, from the staging data repository, the data identified as being from the first participant in the first multi-participant survey to the first study data repository and the data identified as being from the second participant in the second multi-participant survey to the second study data repository. In some embodiments, the system further comprises computer readable instructions for transferring, from the staging data repository, the data identified as being from the first multi-participant survey to the first study data repository and the data identified as being from the second multi-participant survey to the second study data repository.

In some embodiments, the system further comprises computer readable instructions for locking at least one of the plurality of study data repositories. In some embodiments, the plurality of study data repositories comprise at least 2, 3, 4, 5, 6, 7, 8, 9, 10, 50, 100, 1000, 10,000, 100,000, or 1,000,000 study data repositories. In some embodiments, the plurality of multi-participant surveys is a plurality of clinical trials. In some embodiments, the plurality of multi-participant surveys is a plurality of market research surveys. In some embodiments, the plurality of multi-participant surveys is a plurality of political research surveys.

In some embodiments, the electronic device is located at a site. In some embodiments, the site is a hospital, medical clinic, or laboratory. In some embodiments, the electronic device accepts data from a plurality of participants that communicates with the site through in-person visits. In some embodiments, the electronic device accepts data from a plurality of participants that communicates with the site electronically. In some embodiments, the electronic communication comprises an e-mail, text, telephone call, or voice message.

In some embodiments, data identified as being from the first participant in the first multi-participant study is transferred from the staging data repository to the second study data repository, and the system comprises computer readable instructions for transferring, from the second study data repository to the first study data repository, the data identified as being from the first participant in the first multi-participant study that was transferred from the staging data repository to the second study data repository.

In another aspect, a system for managing data from a plurality of multi-participant surveys is provided, said system comprising: a) an electronic device, wherein said electronic device comprises: i.) logic for receiving data from a first participant in a first multi-participant survey, wherein the data from the first participant are identified for analysis as being from the first participant or as being from the first multi-participant survey; ii.) logic for receiving data from a second participant in a second multi-participant survey into the electronic device, wherein the first multi-participant survey is different from the second multi-participant survey, and wherein the data from the second participant are identified for analysis as being from the second participant or as being from the second multi-participant survey; iii.) logic for aggregating the data from the first participant or the data from the first multi-participant survey for analysis; iv.) logic for aggregating the data from the second participant or the data from the second multi-participant survey for analysis; and v.) storage adapted to store the aggregated data from the first participant or the data from the first multi-participant survey and the aggregated data from the second participant or the data from the second multi-participant survey; b) a staging data repository comprising: i.) an interface for communication with said electronic device; ii.) logic for receiving data from said electronic device through said communication interface; iii.) storage adapted to receive the aggregated data from the first participant or the data from the first multi-participant survey and the aggregated data from the second participant or the data from the second multi-participant survey; and c) a plurality of study data repositories, where the plurality of study data repositories comprise i.) an interface for communication with said staging data repository; ii.) logic for receiving data from said staging data repository; and iii.) logic for processing data from said staging data repository.

In some embodiments, the data from the first participant comprise data from the first multi-participant survey, and the data from the second participant comprise data from the second multi-participant survey. In some embodiments, the electronic device comprises logic for recording the data from the first participant in the first multi-participant survey and the data from the second participant in the second multi-participant survey on the electronic device.

In some embodiments, the electronic device is not a handheld electronic device. In some embodiments, the device is a workstation. In some embodiments, the electronic device is a handheld electronic device. In some embodiments, the handheld electronic device is a personal digital assistant, tablet computer, or a telephone. In some embodiments, the electronic device is connected to the Internet.

In some embodiments, the logic comprises electronic circuitry. In some embodiments, the logic comprises computer program code. In some embodiments, the logic comprises electronic circuitry and computer program code.

In some embodiments, the first multi-participant survey and the second multi-participant survey are concurrent. In some embodiments, the first multi-participant survey ends before the second multi-participant survey begins. In some embodiments, the first participant and the second participant are the same person. In some embodiments, the first participant and the second participant are different people. In some embodiments, the first participant enters the data from the first multi-participant survey into the electronic device, and the second participant enters the data from the second multi-participant survey into the electronic device.

In some embodiments, a first individual enters the data from the first participant in the first multi-participant survey into the device, and a second individual enters the data from second participant in the second multi-participant survey into the device. In some embodiments, the first individual is a healthcare provider and the second individual is a healthcare provider. In some embodiments, the first individual and the second individual are the same healthcare provider. In some embodiments, the electronic device further comprises logic for receiving data from at least 2, 3, 4, 5, 6, 7, 8, 9, 10, 50, 100, 1000, 10,000, 100,000, or 1,000,000 or more multi-participant surveys into the electronic device.

In some embodiments, the data identified as being from the first participant in the first multi-participant survey is transmitted to the staging data repository and the data identified as being from the second participant in the second multi-participant survey is transmitted to the staging data repository. In some embodiments, the data identified as being from the first multi-participant survey is transmitted to the staging data repository and the data identified as being from the second multi-participant survey is transmitted to the staging data repository. In some embodiments, the data identified as being from the first participant in the first multi-participant survey is transferred from the staging data repository to the first study data repository and the data identified as being from the second participant in the second multi-participant survey is transferred from the staging data repository to the second study data repository.

In some embodiments, the data identified as being from the first multi-participant survey is transferred from the staging data repository to the first study data repository and the data identified as being from the second multi-participant survey is transferred from the staging data repository to the second study data repository. In some embodiments, at least one of the plurality of study data repositories is locked. In some embodiments, a new study data repository is added to the plurality of study data repositories, wherein the new study data repository is in electronic communication with the staging data repository. In some embodiments, the plurality of study data repositories comprise at least 2, 3, 4, 5, 6, 7, 8, 9, 10, 50, 100, 1000, 10,000, 100,000, or 1,000,000 study data repositories.

In some embodiments, the plurality of multi-participant surveys is a plurality of clinical trials. In some embodiments, the plurality of multi-participant surveys is a plurality of market research surveys. In some embodiments, the plurality of multi-participant surveys is a plurality of political research surveys.

In some embodiments, the electronic device is provided to a site, wherein a plurality of participants communicates with the site. In some embodiments, the site is a hospital, medical clinic, or laboratory. In some embodiments, the plurality of participants communicates with the site through in-person visits. In some embodiments, the plurality of participants communicates with the site electronically. In some embodiments, the electronic communication comprises an e-mail, text, telephone call, or voice message. In some embodiments, the electronic device is provided to the first participant. In some embodiments, a plurality of participants participates in the first multi-participant survey and a plurality of participants participates in the second multi-participant survey.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features are set forth with particularity in the appended claims. A better understanding of the features and advantages will be obtained by reference to the following detailed description that sets forth illustrative embodiments and the accompanying drawings of which:

DETAILED DESCRIPTION OF THE INVENTION

Overview

In general, devices, methods, computer readable medium, and systems are provided herein for managing data on an electronic device, wherein the data can be from a plurality of multi-participant surveys (e.g., clinical trials). Data from a plurality of multi-participant surveys can be entered, identified for further analysis, and/or aggregated on one or more electronic devices. In some cases, unique protocol or study identification is applied to data (e.g., subject data) each time data is entered into a device. In some cases, the subject is a patient in a study, e.g., a clinical trial. One or more devices can be used to collect data for one or more multi-participant studies and/or protocols within a study. The devices, methods, computer readable medium, and systems provided herein can transfer data from a plurality of multi-participant surveys on one or more electronic devices to a staging data repository. Data in a staging data repository can be transferred (sifted) from the staging data repository to one or more study data repositories. The transfer of data from a staging data repository to a study data repository can be based on identifying information of a participant in a multi-participant survey and/or information identifying the multi-participant survey. The identifying information can be captured when datum or data are entered into a device.

The computer-readable medium described herein can be non-transitory. Non-transitory computer-readable media can comprise all computer-readable media, with the sole exception being a transitory, propagating signal.

Figure 1B:
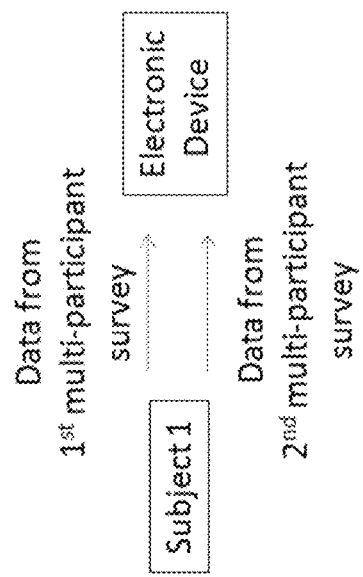
FIG. 1A and FIG. 1B illustrate entry of data from a plurality of multi-participant surveys into an electronic device.
Figure 1A:
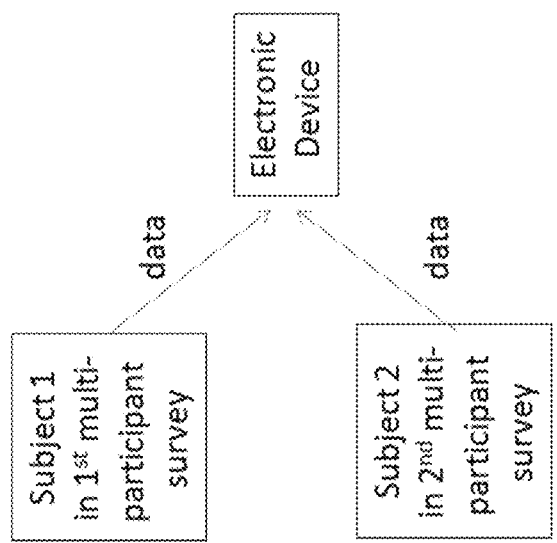

In one embodiment, multiple subjects can enter data from different multi-participant surveys into an electronic device. For example, FIG. 1A illustrates a first subject in a first multi-participant survey entering data into an electronic device, and a second subject in a second multi-participant survey entering data into the electronic device. In some cases, a plurality of subjects (e.g., greater than 10, greater than 100, greater than 1000, greater than 10,000, greater than 100,000, or greater than 1,000,000) enters data into the electronic device. In some cases, about 100 to about 1000, about 1000 to about 10,000, about 10,000 to about 100,000, or about 100,000 to about 1,000,000 subjects enter data into an electronic device. In another embodiment, a single subject in a plurality of multi-participant surveys can enter data from the plurality of multi-participant surveys into an electronic device. For example, FIG. 1B illustrates a first subject in a first multi-participant survey and a second multi-participant survey entering data from the first multi-participant survey and the second multi-participant survey into an electronic device. In some cases, a subject enters data from a plurality of multi-participant surveys (e.g., greater than 10, greater than 100, greater than 1000, greater than 10,000, greater than 100,000, or greater than 1,000,000) into an electronic device. In some cases, a subject enters data from about 10 to about 100, about 100 to about 1000, about 1000 to about 10,000, about 10,000 to about 100,000, or about 100,000 to about 1,000,000 multi-participant surveys into an electronic device.

In some cases, each subject in a multi-participant survey enters data into a separate electronic device. In some cases, each subject in a multi-participant survey has, or is provided, an electronic device, e.g., a portable electronic device, e.g., a handheld electronic device. In some cases, about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 electronic devices are used, or provided to subjects in one or more multi-participant surveys. In some cases, about 2 to about 10, about 10 to about 100, about 100 to about 1000, about 1000 to about 10,000, about 10,000 to about 100,000, about 100,000 to about 1,000,000, about 1,000,000 to about 10,000,000, about 10,000,000 to about 100,000,000 electronic devices are used, or provided to subjects in one or more multi-participant studies.

In one aspect, a method for managing data on an electronic device is provided herein, wherein the data are from a plurality of multi-participant surveys, and wherein the data are managed for analysis. The method can comprise entering data from a first participant in a first multi-participant survey into the electronic device, wherein the data from the first participant is identified for analysis as being from the first participant and/or as being from the first multi-participant survey. The method can comprise entering data from a second participant in a second multi-participant survey into the electronic device, wherein the first multi-participant survey is different from the second multi-participant survey, and wherein the data from the second participant is identified for analysis as being from the second participant and/or as being from the second multi-participant survey. The method can comprise aggregating the data from the first participant or the data from the first multi-participant survey for analysis, and aggregating the data from the second participant or the data from the second multi-participant survey for analysis. In some cases, data from a plurality of multi-participant surveys (e.g., greater than 10, greater than 100, greater than 1000, greater than 10,000, greater than 100,000, or greater than 1,000,000) are aggregated; in some cases, data from a plurality of subjects (e.g., greater than 10, greater than 100, greater than 1000, greater than 10,000, greater than 100,000, or greater than 1,000,000) are aggregated. In some cases, data from about 10 to about 100, about 100 to about 1000, about 1000 to about 10,000, about 10,000 to about 100,000, or about 100,000 to about 1,000,000 multi-participant surveys are aggregated. In some cases, data from about 10 to about 100, about 100 to about 1000, about 1000 to about 10,000, about 10,000 to about 100,000, or about 100,000 to about 1,000,000 subjects are aggregated.

In another aspect, a computer readable medium is provided herein having stored thereon sequences of instructions. The instructions, when executed by a computer system, can cause the computer system to accept data from a first participant in a first multi-participant survey in an electronic device, wherein the data from the first participant is identified for analysis as being from the first participant and/or as being from the first multi-participant survey. The instructions can cause the computer system to accept data from a second participant in a second multi-participant survey in the electronic device, wherein the first multi-participant survey is different from the second multi-participant survey, and wherein the data from the second participant is identified for analysis as being from the second participant or as being from the second multi-participant survey. The instructions can cause the computer system to aggregate the data from the first participant and/or the data from the first multi-participant survey for analysis, and aggregate the data from the second participant and/or the data from the second multi-participant survey for analysis. In some cases, data from a plurality of multi-participant surveys (e.g., greater than 10, greater than 100, greater than 1000, greater than 10,000, greater than 100,000, or greater than 1,000,000) are aggregated; in some cases, data from a plurality of subjects (e.g., greater than 10, greater than 100, greater than 1000, greater than 10,000, greater than 100,000, or greater than 1,000,000) are aggregated. In some cases, data from about 10 to about 100, about 100 to about 1000, about 1000 to about 10,000, about 10,000 to about 100,000, or about 100,000 to about 1,000,000 multi-participant surveys are aggregated. In some cases, data from about 10 to about 100, about 100 to about 1000, about 1000 to about 10,000, about 10,000 to about 100,000, or about 100,000 to about 1,000,000 subjects are aggregated.

In another aspect, a system for managing data from a plurality of multi-participant surveys is provided herein. The system can comprise computer readable instructions for accepting data from a first participant in a first multi-participant survey in an electronic device. The data from the first participant can be identified for analysis as being from the first participant and/or as being from the first multi-participant survey. The system can comprise computer readable instructions for accepting data from a second participant in a second multi-participant survey in the electronic device. The first multi-participant survey can be different from the second multi-participant survey. The data from the second participant can be identified for analysis as being from the second participant and/or as being from the second multi-participant survey. The system can comprise computer readable instructions for aggregating the data from the first participant and/or the data from the first multi-participant survey for analysis, and aggregating the data from the second participant and/or the data from the second multi-participant survey for analysis. In one embodiment, the data from the first participant can comprise data from the first multi-participant survey, and the data from the second participant can comprise data from the second multi-participant survey. In some cases, data from a plurality of multi-participant surveys (e.g., greater than 10, greater than 100, greater than 1000, greater than 10,000, greater than 100,000, or greater than 1,000,000) are aggregated; in some cases, data from a plurality of subjects (e.g., greater than 10, greater than 100, or greater than 1000, greater than 10,000, greater than 100,000, or greater than 1,000,000) are aggregated. In some cases, data from about 10 to about 100, about 100 to about 1000, about 1000 to about 10,000, about 10,000 to about 100,000, or about 100,000 to about 1,000,000 multi-participant surveys are aggregated. In some cases, data from about 10 to about 100, about 100 to about 1000, about 1000 to about 10,000, about 10,000 to about 100,000, or about 100,000 to about 1,000,000 subjects are aggregated.

Electronic Devices

An electronic device used in the methods and systems described herein can be adapted for use by a subject and/or third party (e.g., clinical staff) for viewing and/or inputting information. In one embodiment, the electronic device is a portable electronic device. The portable electronic device can be a handheld electronic device. The handheld device can be small enough to put into a pocket or purse. The handheld electronic device can be, e.g., a phone and/or personal digital assistant (PDA), cell phone, smartphone, mobile internet device, enterprise digital assistant, data capture mobile device, batch terminal, portable media player, feature phone, personal navigation device, Palm device (e.g., Palm Pilot, Palm TX), Pocket PC (Windows Mobile Classic device), or pager.

In one embodiment, the handheld electronic device is a smartphone. The smartphone can be manufactured by, e.g., Acer, Apple, Asus, AT&T, Blackberry, BLU products, Casio Inc., Dell Inc., Garmin-Asus, Hewlett-Packard (HP), HTC, Huawei Technologies col, Ltd., Kyocera, LG, Motorola, Nokia, Palm, Pantech & Curitel, Pharos, Samsung, Scosche Industries, Inc., Sharp, Sonim Technologies, Sony Ericsson, Sprint, Audiovox/UTStarcom, ZTE, or ZyXEL. The smartphone can comprise an operating system, and the operating system can be, e.g., Android (Google), Windows Mobile (Microsoft), Windows Phone (Microsoft), Symbian (Nokia), Blackberry OS (RIM), iOS (Apple), or a Linux-based system, e.g., Maemo, or MeeGo.

In one embodiment, the electronic device is an iPhone, iPhone 4S, iPhone 4, iPhone 3GS, iPhone 5, Sharp FX Plus, Palm Pixi Plus, HTC Status, LG Phoenix, Pantech Crossover, Samsung Captivate, Impulse 4G, Samsung Focu, Motorola Atrix, Sony Ericsson Xperia, HTC Inspire, Samsung Infuse, HTC HD7S, LG Thrill, Samsung Galaxy S II, HP iPAQ, HP iPAQ smartphone, HP iPAQ PDA, Nokia E7-00, Nokia E6-00, Nokia X3-02, Nokia C3-01, BlackBerry Bold, Blackberry 9850, Blackberry Torch, Blackberry Curve, BlackBerry Pearl, Samsung Stratosphere, HTC Rhyme, Motorola Droid Bionic, Pantech Breakout, LG Enlighten, Motorola Droid, LG Revolution, etc.

The electronic device used in the methods and systems described herein can be a computer. The computer can be, e.g., a personal computer, minicomputer, mainframe, multiprocessor system, network computer, processor-based electronic device, desktop computer, laptop computer, PC computer, Macintosh computer, notebook computer, netbook computer, e-reader, tablet computer, or tablet PC. In one embodiment, the electronic device is a tablet computer. The tablet computer can be, e.g., an iPad or iPad 2. The computer can comprise an operating system. The operating system (OS) for the computer can be, e.g., Android, iOS, Linux, Mac OS X, Microsoft Windows, or Microsoft Windows XP. The operating system can be a real-time, multi-user, single-user, multi-tasking, single tasking, distributed, or embedded.

The electronic device can have one or more visual, audible, or tactile features for communicating with the user or subject. For example, the electronic device can communicate with a user by, e.g., vibration, e-mail, text messaging, voice mail, phone call, or print out. The electronic device can comprise pre-defined alerts that can remind a user to enter data into the electronic device. The electronic device can be configured to communicate with a user, by text or audibly, in one or more of a number of different languages, e.g., English, Spanish, Welsh, Scots Gaelic, German, French, Italian, Swedish, Castilian Spanish, Catalan, Galician, Basque, Portuguese, Polish, Arabic, Russian, Hindi, Greek, Finnish, Danish, Czech, Croatian, Mandarin Chinese, Cantonese, or Flemish. Alerts provided by the electronic device can ensure at least 60%, 65%, 70%, 75%, 80%, 85%, 90%, 95%, or 100% compliance with protocol requirements for a multi-participant survey.

The electronic device can be configured to accept a response to multiple data collection options, e.g., scales, different questions type, e.g., quality of life (QoL) assessments, etc. The electronic device can be capable of automatic software uploads.

The electronic device can also include one or more input and output (I/O) devices such as a mouse, game input device or controller, display, touch screen or other I/O device or devices in various combinations. The electronic device can comprise one or more other display and data input features that a user can use to interface with the electronic device. An input feature can be, e.g., a keyboard, mouse, touch-sensitive screen, tap-and-touch based interface, dial, button, trackball, light pen, digitizer pen, stylus or other pointing device, microphone, joystick, or voice recognition feature. The electronic device can have a display screen with touch input and/or a miniature keyboard. A display screen can about, at least, less than, or more than 1, 2, 2.5, 3, 3.5, 4, 4.5, 5, 5.5, 6, 6.5, 7, 7.5, 8, 8.5, 9, 9.5, 10, 10.5, 11, 11.5, 12, 12.1, 12.5, 13, 13.5, 14, 14.5, 15, 15.5, 16, 16.5, 17, 17.5, 18, 18.5, 19, 19.5, or 20 inches in diameter, and can be in the landscape or portrait configuration. The electronic device can be connected to an output device, such as a printer.

The electronic device can comprise other features, such as a digital still camera, digital video camera, calendar, speaker, clock, GPS capability, Bluetooth technology, or cloud computing capability. The electronic device can comprise a smart card reader, radio-frequency identification (RFID), or barcode. The electronic device can comprise a webbrowser, portable media player, camera, Wi-Fi, and mobile broadband access.

In some cases, about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 electronic devices are used, or provided to subjects in one or more multi-participant surveys. In some cases, about 2 to about 10, about 10 to about 100, about 100 to about 1000, about 1000 to about 10,000, about 10,000 to about 100,000, about 100,000 to about 1,000,000, about 1,000,000 to about 10,000,000, about 10,000,000 to about 100,000,000 electronic devices are used, or provided to subjects in one or more multi-participant studies.

In some embodiments, the electronic device is not a portable electronic device. In some embodiments, the electronic device is not a handheld electronic device. For example, the electronic device can be a workstation.

The electronic device can be adapted to communicate with at least one other computer via a wireless connection or via a wired connection, including the use of a modem and/or a network, such as a LAN or the Internet. Other networks can include, e.g. cellular communication networks, Packet Data Networks (PDNs), 4 G network, 3 G communications, or Public Switched Telephone Network (PSTNs). The electronic device can comprise integrated IEEE 802.11b/g.

Written instructions, in hardcopy or electronic form, can be provided to a user of an electronic device. The instructions can describe one or more methods of operating the electronic device.

The electronic device can be a patient-reported outcome (PRO) instrument. The PRO instrument can be configured to satisfy Food and Drug Administration (FDA) guidelines for patient-reported outcome measures.

In one embodiment, digital rights management control (including control of access rights and data flow paths) can be incorporated into the device to protect the privacy of subject data and/or medical history information, e.g., in accordance with regulatory standards such as the Health Insurance Portability and Accountability Act (HIPAA).

The electronic device can present one or more questions to a user. The one or more questions can be presented audibly or on a display. The one or more questions can be part of a multi-participant survey. In one embodiment, only one question appears on the display at a time. In another embodiment, more than one question appears on the display at a time, e.g., 2, 3, 4, 5, 6, 7, 8, 9, 10, 11, 12, 13, 14, 15, 16, 17, 18, 19, 20 or more questions. In some embodiments, screen splitting can be used on the electronic device. In one embodiment, instructions for a questionnaire can be placed on an introductory screen, and then questions are presented one per screen. In another embodiment, the text to a question is placed on one screen, and one or more response options are placed on a subsequent screen. In another embodiment, the same information can be presented on multiple screens. In another embodiment, a screen can have a supplementary "pop-up." In one embodiment, the information on a display of the electronic device can be presented similar to a hard-copy paper. In another embodiment, a full A4 size electronic device can allow reproduction of a paper page. In some cases, a user can adjust the display. For example, the user can adjust the text size, brightness, contrast, text font, etc.

The electronic device can restrict entries by a user to only those entries that are in a valid range. In one embodiment, data are not accepted by the device until all data are entered in the device. The valid range can be a numerical range. In some embodiments, entry of the data is restricted based on time of day, time or week, time of year, drug administration history or schedule, or location of a subject (e.g., based on use of GPS, for example).

The devices, systems, computer readable medium, and methods described herein can be implemented in or upon a computer system. A computer system can include various combinations of a central processor or other processing device, an internal communication bus, various types of memory or storage media (RAM, ROM, EEPROM, cache memory, disk drives, etc.) for code and data storage, and one or more network interface cards or ports for communication purposes. The devices, systems, and methods described herein may include or be implemented in software code, which may run on such computer systems or other systems. For example, the software code can be executable by a computer system, for example, that functions as the storage server or proxy server, and/or that functions as a user's terminal device. During operation the code can be stored within the computer system. At other times, the code can be stored at other locations and/or transmitted for loading into the appropriate computer system. Execution of the code by a processor of the computer system can enable the computer system to implement the methods and systems described herein.

Figure 5:
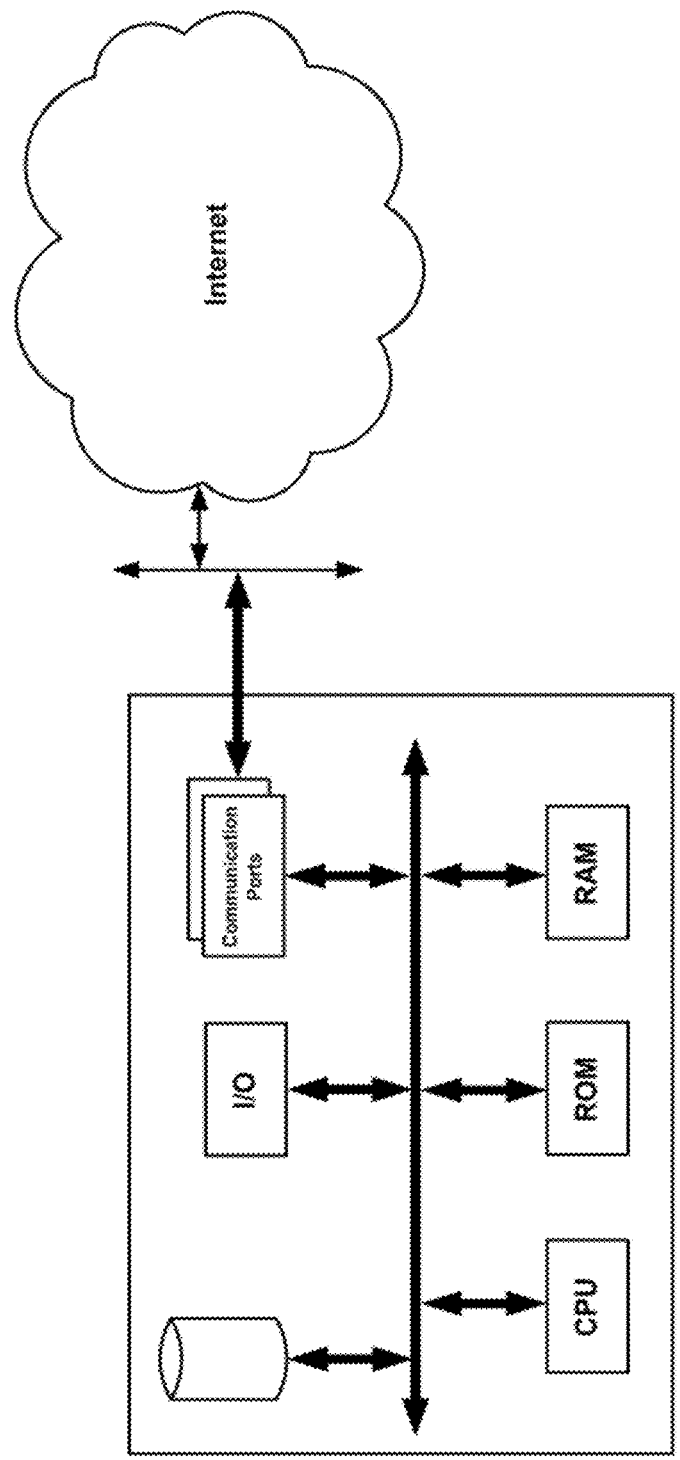
FIG. 5 illustrates an example of a network or host computer platform as can be used to implement a server or electronic devices, according to an embodiment.
Figure 6:
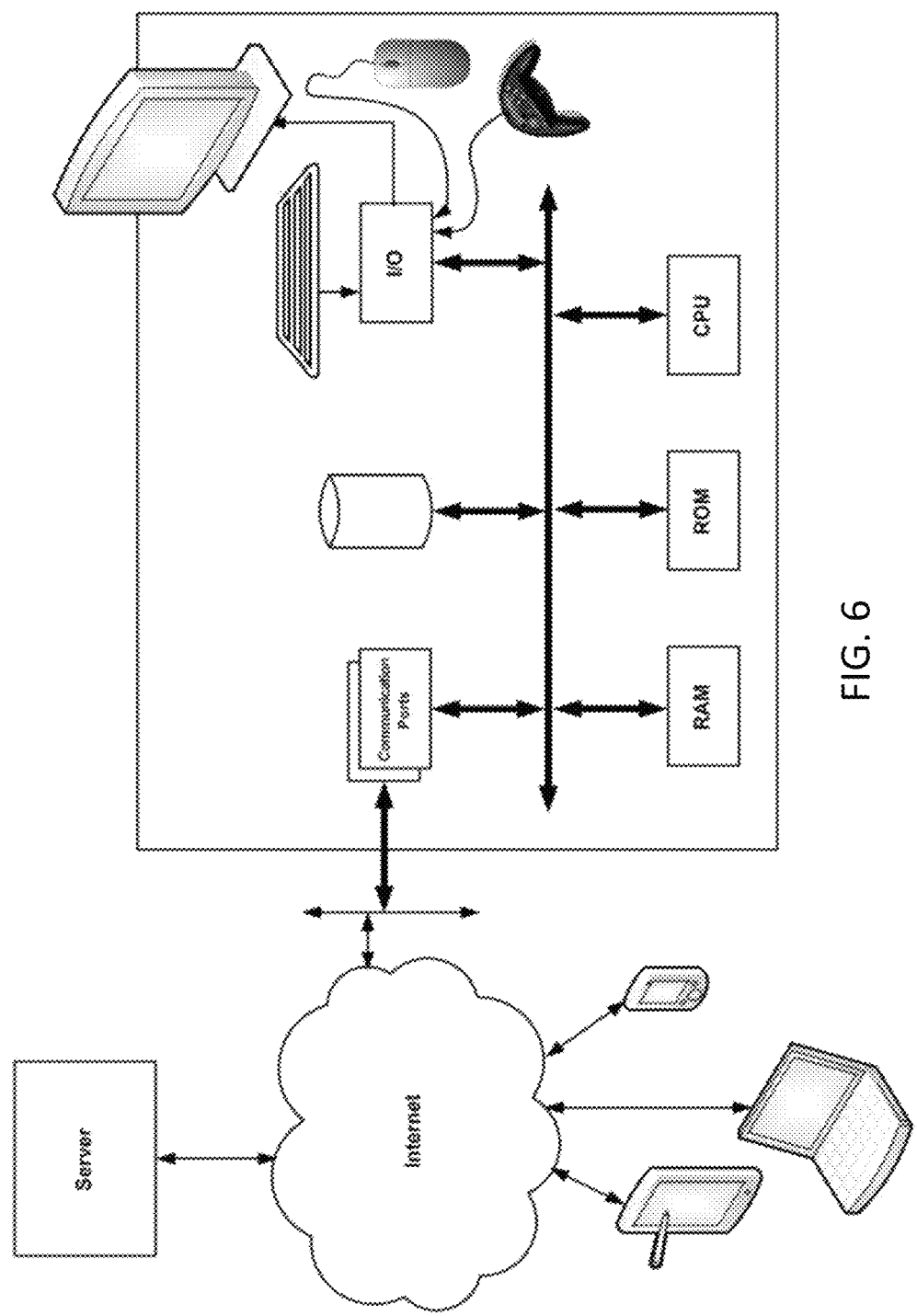
FIG. 6 depicts a computer or electronic device with user interface elements, as can be used to implement a personal computer, electronic device, or other type of work station or terminal device according to an embodiment, although the computer or electronic device of FIG. 6 can also act as a server if appropriately programmed.

FIG. 5 and FIG. 6 provide examples of functional block diagram illustrations of computer hardware platforms. FIG. 5 shows an example of a network or host computer platform, as can be used to implement a server or electronic devices, according to an embodiment. FIG. 6 depicts a computer or electronic device with user interface elements, as can be used to implement a personal computer, electronic device, or other type of work station or terminal device according to an embodiment, although the computer or electronic device of FIG. 6 can also act as a server if appropriately programmed. The systems and methods described herein can be implemented in or upon such computer hardware platforms in whole, in part, or in combination. The systems and methods described herein, however, are not limited to use in such systems and can be implemented or used in connection with other systems, hardware or architectures. The methods described herein can be implemented in computer software that can be stored in the computer systems, electronic devices, and servers described herein.

A computer system, electronic device or server, according to various embodiments, can include a data communication interface for packet data communication. The computer system, electronic device, or server can also include a central processing unit (CPU), in the form of one or more processors, for executing program instructions. The computer system, electronic device, or server can include an internal communication bus, program storage and data storage for various data files to be processed and/or communicated by the server, although the computer system or server can receive programming and data via network communications. The computer system, electronic device, or server can include various hardware elements, operating systems and programming languages. The electronic device, server or computing functions can be implemented in various distributed fashions, such as on a number of similar or other platforms.

The methods described herein can be implemented in mobile devices such as mobile phones, mobile tablets and other mobile devices with various communication capabilities including wireless communications, which may include radio frequency transmission, infrared transmission or other communication technology. Thus, the hardware described herein may include one or more transmitters and receivers for radio and/or other communication technology and/or interfaces to couple to and communication with communication networks.

The methods described herein can be implemented in computer software that can be stored in the computer systems or electronic devices including a plurality of computer systems and servers. These can be coupled over computer networks including the internet. Accordingly, an embodiment includes a network including the various system and devices coupled with the network.

Further, various methods and architectures as described herein, such as the various processes described herein or other processes or architectures, can be implemented in resources including computer software such as computer executable code embodied in a computer readable medium, or in electrical circuitry, or in combinations of computer software and electronic circuitry.

Aspects of the devices, systems, and methods described herein can be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the devices, systems, and methods include: microcontrollers with memory, embedded microprocessors, firmware, software, etc. Furthermore, aspects of the devices, systems, and methods can be embodied in microprocessors having software-based circuit emulation, discrete logic (sequential and combinatorial), custom devices, fuzzy (neural network) logic, quantum devices, and hybrids of any of the above device types. Of course the underlying device technologies can be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

The various functions or processes disclosed herein can be described as data and/or instructions embodied in various computer-readable media, in terms of their behavioral, register transfer, logic component, transistor, layout geometries, and/or other characteristics. Computer-readable media in which such formatted data and/or instructions can be embodied include, but are not limited to, non-volatile storage media in various forms (e.g., optical, magnetic or semiconductor storage media, hard disk, optical disk, magneto-optical disk), volatile media (e.g., dynamic memories) and carrier waves that can be used to transfer such formatted data and/or instructions through wireless, optical, or wired signaling media, transmission media (e.g., coaxial cables, copper wire, fibers optics) or any combination thereof. Examples of transfers of such formatted data and/or instructions by carrier waves include, but are not limited to, transfers (uploads, downloads, email, etc.) over the Internet and/or other computer networks via one or more data transfer protocols (e.g., HTTP, FTP, SMTP, etc.). Transmission media can include acoustic, optical, or electromagnetic waves, e.g., such as those generated during, e.g., radio frequency (RF) communications or infrared data communications. When received within a computer system via one or more computer-readable media, such data and/or instruction-based expressions of components and/or processes under the systems and methods can be processed by a processing entity (e.g., one or more processors) within the computer system in conjunction with execution of one or more other computer programs.

Processing, computing, calculating, determining, or the like, can refer in whole or in part to the action and/or processes of a processor, computer or computing system, or similar electronic computing device, that manipulate and/or transform data represented as physical, such as electronic, quantities within the system's registers and/or memories into other data similarly represented as physical quantities within the system's memories, registers or other such information storage, transmission or display devices. Users can be individuals as well as corporations and other legal entities. Furthermore, the processes presented herein are not inherently related to any particular computer, processing device, article or other apparatus. An example of a structure for a variety of these systems will appear from the description herein. Embodiments of the invention are not described with reference to any particular processor, programming language, machine code, etc. A variety of programming languages, machine codes, etc. can be used to implement the teachings of the invention as described herein.

Authentication

Authentication of a user can be required before a user is able to use, or initiate application software of, an electronic device. Methods of initiating application software are described, e.g., in U.S. Pat. No. 7,783,072. In one embodiment, a user can initiate application software, e.g., by double clicking a desktop icon on a computer system using a mouse. A user identification module on a local system can begin to authenticate the user of the software application. The user identification module can comprise a login screen prompting user entry into fields such as, e.g., a username, a password, and/or passcode. A username and password can be assigned to the user, or the user can choose a username and password.

An electronic device can be configured to accept data from one or more specific individuals. Identifying information can be required to be entered into an electronic device before the electronic device will accept data from the individual. The identifying information can comprise, e.g., date of birth, social security number, location of birth, mother's maiden name, grandparent's name, driver's license number, or state identification number.

In one embodiment, asymmetric key cryptography (public-key cryptography) can be used to authenticate a user. The embodiment can employ a public key and a private key, which can be related mathematically. Asymmetric cryptography differs from symmetric cryptography in that in asymmetric cryptography a user does not have to share the private key. A token device, such as a smartcard or an eToken, can be used in such an exemplary public-key cryptography authentication. The use of such token devices and public-key cryptography to authenticate a user are well known in the field, and any such token device available can be used. For example, a user can log on and the user's public key and private key (which remains secret to the user) can encrypt the logon. The encryption can be transmitted to an external device, which also houses a copy of the user's public key. The external device can then decrypt the encryption, thereby verifying the user's identity, or authenticating the user.

A smart card can be used to authenticate a user. A smart card can be the size of a credit card, and can possess a processor and/or a memory that can exchange data with a computer system. A smart card can have an embedded Integrated Circuit (IC). The IC can be a logic circuit with its associated memories or a microcontroller with its associated memories and software, or a microcontroller with its associated memories and software coupled to a custom circuit block or interface. In one embodiment, a smart card can provide a processor and/or memory in a silicon-based integrated circuit. A smart card can include electronic or optical interfaces to exchange data with a computer system and can be powered by a battery or other power source.

In another embodiment, biometrics can be used to authenticate a user, e.g., either by providing the user's private key or both the private key and password. Biometrics can include a method of verifying an individual's identity based on a measurement of an individual's physical feature or repeatable actions where those features and/or actions are both unique to that individual and measurable. Biometrics can include the use of, e.g., voice, speech, fingerprint, retina, iris, hand geometry, facial recognition, handwritten signature, genetic material, or veins, nucleic acid (e.g., DNA or RNA), protein sample, and/or blood sample. In one embodiment, an identification module can comprise a biometric recognition, such that the biometric recognition comprises the user's username and passcode. In another embodiment, the biometric recognition can comprise the user's username, and then the electronic device can prompt the user for a passcode.

In another embodiment, private and public keys and/or username and password can be periodically changed to prevent unauthorized users from gaining access to the local system. A username or public key can also be deactivated, such as if a token device is reported missing or stolen.

Requiring a username and passcode, or public and private key, to authenticate a user can comply with the requirements for an electronic signature under 21 C.F.R. Part 11, which states in relevant part that electronic signatures which are not based on biometrics shall employ at least two distinct identification components, such as an identification code and password.

A username and password can be provided by the user to initially login to an application on an electronic device. A local system can then transmit the user-provided username and password to a user authentication module on an external device. The external device can be a computer system, such as a personal computer, or can be a server. The external device can comprise a database which comprises a plurality of stored usernames and passcodes. The username and passcode can be assigned to a user upon account activation, or when a user first installs the software application.

An electronic device can be provided to a site, e.g., a clinic, hospital, medical center, laboratory, etc. A plurality of participants can communicate with the site. For example, the plurality of participants can communicate with the site through in-person visits. The plurality of participants can communicate with the site electronically. The electronic communication can be, e.g., an e-mail, a text, a telephone call, or a voice message. An electronic device can be provided to a participant, who can possess the electronic device for a period of time (e.g., days, weeks, months, years, or decades).

An electronic device can communicate with other electronic devices, for example, over a network. An electronic device can communicate with an external device (e.g., staging data repository) using a variety of communication protocols. A set of standardized rules, referred to as a protocol, can be used utilized to enable electronic devices to communicate. In one embodiment, the communications protocol used is HTTP ("Hypertext Transfer Protocol"). HTTP can be an application-level protocol used in connecting servers and users on the World-Wide Web (WWW). HTTP can be based on a request-response mechanism and can use TCP ("Transmission Control Protocol") connections to transfer data. In another embodiment, HTTPS ("Hypertext Transfer Protocol Secure"), a variant of HTTP that can implement the SSL ("Secure Sockets Layer") mechanism, is used. SSL can be a standard protocol for implementing cryptography and enabling secure transactions on the Web.

SSL can use public key signatures and digital certificates to authenticate a server and user and can provide an encrypted connection for the user and server to exchange messages securely. When HTTPS is the protocol used, the URL (Uniform Resource Locator) defining the HTTPS request is directed to a secure port number instead of a default port number to which an HTTP request is directed. Other protocols can be used to transfer data, for example without limitation, FTP or NFS.

An electronic device can be connected to a staging data repository and/or server through, e.g., a network. A network can be a small system that is physically connected by cables or via wireless communication (a local area network or "LAN"). An electronic device can be a part of several separate networks that are connected together to form a larger network (a wide area network or "WAN"). Other types of networks of which an electronic device can be a part of include the internet, telcom networks, intranets, extranets, wireless networks, and other networks over which electronic, digital and/or analog data can be communicated.

Communication between the electronic device and an external device, e.g., staging data repository, can be accomplished wirelessly. Such wireless communication can be Bluetooth or RTM technology. In one embodiment, a wireless connection can be established using exemplary wireless networks such as cellular, satellite, or pager networks, GPRS, or a local data transport system such as Ethernet or token ring over a local area network.

A user authentication module can initiate a request to, or query, a database to detect the transmitted username. If the username exists in the database, the user authentication module can query the database for the passcode or password associated with the username and compare it to the transmitted passcode. If the transmitted passcode is the same as the passcode in the database, the user can be successfully authenticated and the software application on the local system will initialize. If the transmitted username is not found in the database or if the transmitted passcode does not match the stored passcode, the software application will not initialize and the user can again be prompted to provide a username and passcode by any of the methods described herein. There can be a limited number of times an authentication can be attempted before a user is locked out of the system. Requiring a passcode to authenticate a user can help prevent fraudulent attempts to login under a user's username and also creates a record keeping or tracking system of when a user attempts to login and the identity of the user.

An electronic device can be in communication with one or more servers. The one or more servers can be an application server, a catalog server, a communication server, an access server, a link server, a data server, a staging server, a database server, a member server, a fax server, a game server, a pedestal server, a micro server, a name server, a remote access server (RAS), a live access server (LAS), a network access server (NAS), a home server, a proxy server, a media server, a nym server, network server, a sound server, file server, mail server, print server, a standalone server, or a web server. A server can be a computer.

One or more databases can be used to store information from an electronic device. The databases can be organized using data structures (e.g., trees, fields, arrays, tables, records, lists) included in one or more memories or storage devices.

Entering and Recording Data

In one embodiment, an electronic device can be configured to accept data from a plurality of multi-participant surveys. In another embodiment, an electronic device configured to receive data from a plurality of multi-participant surveys can be temporarily configured to receive data from a single multi-participant survey. For example, if an electronic device is configured to receive data from two multi-participant surveys, the device can be temporarily configured such that a first subject in a first multi-participant survey is only able to enter data regarding the first multi-participant survey in the device. In one embodiment, it is temporarily not possible to enter data from a second multi-participant survey into the electronic device. The electronic device can appear to the first subject to be able to only accept data for a single multi-participant study when the device is actually configured to receive data for two or more multi-participant surveys. In some cases, the electronic device is configured to receive data from a plurality of multi-participant surveys (e.g., about, more than, less than, or at least 10, 100, 1000, 10,000, 100,000, 1,000,000, 10,000,000, or 100,000,000). In some cases, the subject possessing or generating data does not enter the data into an electronic device; rather, another party can enter the data into the electronic device for the subject or on behalf of the subject.

After a first subject in a first multi-participant survey enters data into an electronic device, the electronic device can be provided to a second subject in a second multi-participant survey, and the second subject in the second multi-participant survey can enter data into the electronic device. The electronic device can be temporarily configured to accept data from only the second subject in the second multi-participant survey. In some cases, the subject possessing or generating data does not enter the data into an electronic device; rather, another party can enter the data into the electronic device for the subject or on behalf of the subject.

In one embodiment, the methods described herein comprise recording data from a first participant in a first multi-participant survey and data from a second participant in a second multi-participant survey on an electronic device. In another embodiment, a computer readable medium provided herein comprises instructions that, when executed by a computer system, cause the computer system to record data from a first participant in a first multi-participant survey and data from a second participant in a second multi-participant survey on an electronic device. In another embodiment, a system provided herein comprises computer readable instructions for recording data from a first participant in a first multi-participant survey and data from a second participant in a second multi-participant survey on an electronic device.

Entering, recording, aggregating, and identifying data can make use of hardware elements including circuitry, software elements including computer code stored on a tangible, machine-readable medium or a combination of hardware and software elements. Software can include, e.g., device drivers, development tools, firmware, application software, or operating systems. An input feature described herein can be used to input data, e.g., a keyboard, mouse, touch-sensitive screen, tap-and-touch based interface, dial, button, trackball, light pen, digitizer pen, stylus or other pointing device, microphone, joystick, or voice recognition feature. The electronic device can have a display screen with touch input and/or a miniature keyboard. In some cases, data are entered into a device in real-time (as the data are generated). Data can be entered into a device after an event.

Data can be identified for analysis by one or more methods. Data can be identified for analysis by individual study (e.g., specific clinical trial), type of study (e.g., clinical trial, consumer survey, political poll), organizer of a study (e.g., academician, college, university, laboratory, hospital, pharmaceutical company, political party, political action committee, non-profit organization), by individual subject, by characteristics of one or more subjects (e.g., age, gender, height, weight, body mass index, blood pressure, blood sugar level, cholesterol level, nationality, ethnicity, race, occupation, residence, citizenship, criminal record, political party affiliation, annual income, highest education level (no high school, some high school, high school graduate, two-year college degree, four-year college degree, graduate degree, doctoral degree, medical degree, law degree), pharmaceutical usage, exercise level, or smoking rate). Data can be electronically "tagged" with one or more of these types of pieces of information in order to be identified for analysis. Data can be identified for analysis using metadata.

Staging Data Repository

Figure 2:
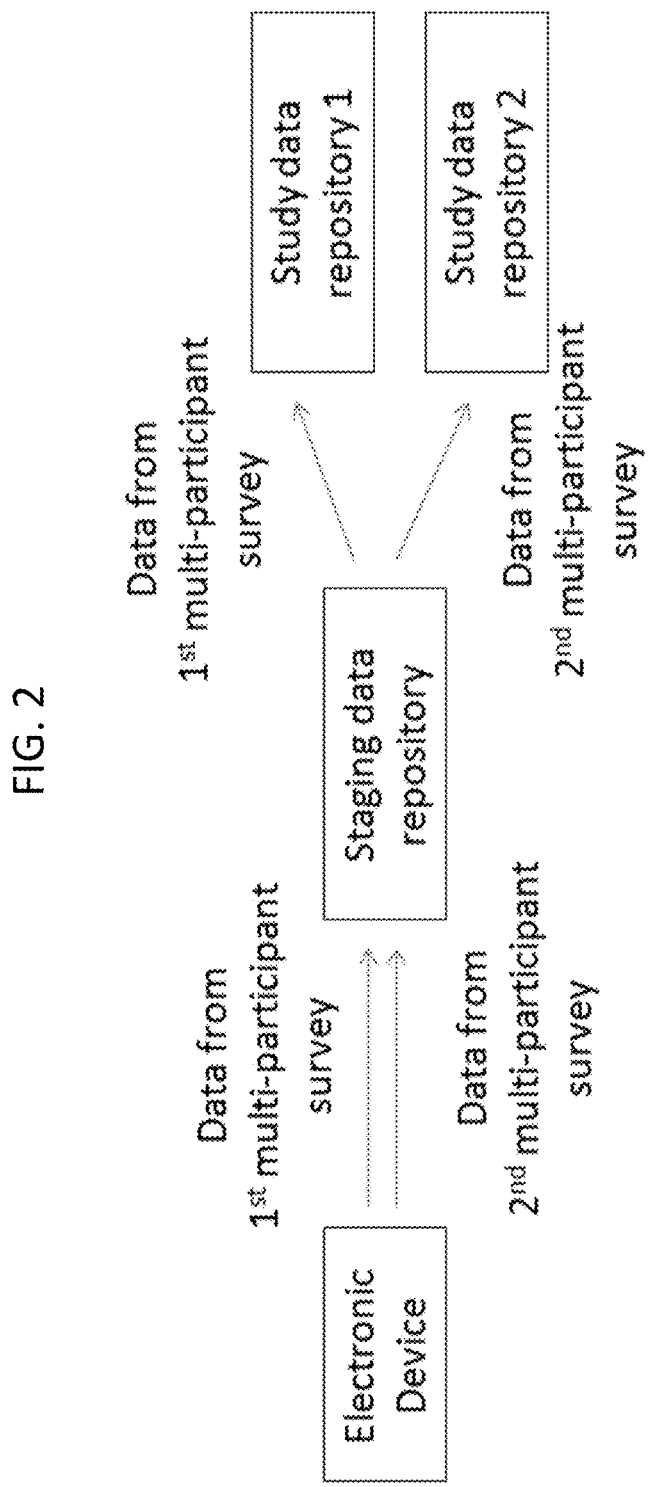
FIG. 2 illustrates transfer of data from a plurality of multi-participant surveys from an electronic device to a staging data repository and transfer of data from a first multi-participant survey to a first study data repository and transfer of data from a second multi-participant survey to a second study data repository.

In one embodiment, an electronic device provided herein is in communication with a staging data repository. The staging data repository can be used to store data from a plurality of multi-participant surveys. In one embodiment, the staging data repository is a server. The staging data repository can communicate with one or more other electronic devices. The staging data repository can comprise data from a plurality of multi-participant surveys. The staging data repository can receive data uploaded from an electronic device. Subject specific and multi-participant survey specific data can be copied from the staging data repository to an appropriate study data repository (see, e.g., FIG. 2). The staging data repository can be hosted on PC-based server software. The staging data repository can be part of a Web-based system.

In some cases, a staging data repository can receive data from about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 electronic devices. In some cases, a staging data repository can receive data from about 2 to about 10, about 10 to about 100, about 100 to about 1000, about 1000 to about 10,000, about 10,000 to about 100,000, about 100,000 to about 1,000,000, about 1,000,000 to about 10,000,000, about 10,000,000 to about 100,000,000 electronic devices.

In some cases, a staging data repository can receive data from about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 multi-participant surveys. In some cases, a staging data repository can receive data from about 2 to about 10, about 10 to about 100, about 100 to about 1000, about 1000 to about 10,000, about 10,000 to about 100,000, about 100,000 to about 1,000,000, about 1,000,000 to about 10,000,000, about 10,000,000 to about 100,000,000 multi-participant surveys.

In some cases, a staging data repository can receive data from about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 subjects, e.g., patients. In some cases, a staging data repository can receive data from about 2 to about 10, about 10 to about 100, about 100 to about 1000, about 1000 to about 10,000, about 10,000 to about 100,000, about 100,000 to about 1,000,000, about 1,000,000 to about 10,000,000, or about 10,000,000 to about 100,000,000 subjects, e.g., patients.

In one embodiment, a method provided herein comprises transmitting data identified as being from a first participant in a first multi-participant survey to a staging data repository and transmitting data identified as being from a second participant in a second multi-participant survey to the staging data repository. The data can be transmitted as a data stream. In another embodiment, a method provided herein comprises transmitting data identified as being from a first multi-participant survey to a staging data repository and transmitting data identified as being from a second multi-participant survey to the staging data repository. Data from a plurality of multi-participant surveys can be transmitted to the staging data repository. Data from a plurality of participants can be transmitted to the staging data repository.

In another embodiment, a computer readable medium provided herein comprises sequences of instructions, which, when executed by a computer system, cause the computer system to transmit data identified as being from a first participant in the first multi-participant survey to a staging data repository and transmit data identified as being from a second participant in the second multi-participant survey to the staging data repository. In another embodiment, a computer readable medium provided herein comprises sequences of instructions, which, when executed by a computer system, cause the computer system to transmit the data identified as being from a first multi-participant survey to a staging data repository and transmit data identified as being from a second multi-participant survey to the staging data repository. Data from a plurality of multi-participant surveys can be transmitted to the staging data repository. Data from a plurality of participants can be transmitted to the staging data repository.

In another embodiment, a system provided herein comprises computer readable instructions for transmitting data identified as being from a first participant in a first multi-participant survey to a staging data repository and transmitting data identified as being from a second participant in the second multi-participant survey to the staging data repository. In another embodiment, a system provided herein comprises computer readable instructions for transmitting data identified as being from a first multi-participant survey to a staging data repository and transmitting data identified as being from a second multi-participant survey to the staging data repository. Data from a plurality of multi-participant surveys can be transmitted to the staging data repository. Data from a plurality of participants can be transmitted to the staging data repository.

In some cases, a plurality of staging data repositories are provided, e.g., about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000. In some cases, the number of staging data repositories provided is about 2 to about 10, about 10 to about 100, about 100 to about 1000, about 1000 to about 10,000, about 10,000 to about 100,000, about 100,000 to about 1,000,000, about 1,000,000 to about 10,000,000, or about 10,000,000 to about 100,000,000.

Study Data Repositories

In another embodiment, a staging data repository is in electronic communication with a plurality of study data repositories. A study data repository can be used to store data specific to an individual and/or specific to a multi-participant study (e.g., clinical trial). The plurality of study data repositories can comprise a first study data repository and a second study data repository. The plurality of study data repositories can comprise about, at least, more than, or less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 5000, 10,000, 100,000, 1,000,000, 10,000,000, or 100,000,000 study data repositories. The plurality of study data repositories can comprise about 2 to about 1000, about 2 to about 500, about 2 to about 100, about 2 to about 50, about 2 to about 25, about 2 to about 10, about 2 to about 5, about 10 to about 1000, about 10 to about 500, about 10 to about 100, about 10 to about 50, about 10 to about 25, or about 10 to about 15 study data repositories. The number of study data repositories can be about 100 to about 1000, about 1000 to about 10,000, about 10,000 to about 100,000, about 100,000 to about 1,000,000, about 1,000,000 to about 10,000,000, or about 10,000,000 to about 100,000,000. In some embodiments, a staging data repository and one or more study data repositories can share the same master database. Two or more data repositories can be synchronized by updating all or part of a study data repository to match a source data repository.

In one embodiment, a method provided herein comprises transferring, from the staging data repository, the data identified as being from a first participant in a first multi-participant survey to a first study data repository and data identified as being from a second participant in a second multi-participant survey to the second study data repository. In another embodiment, a method provided herein comprises transferring, from a staging data repository, data identified as being from a first multi-participant survey to a first study data repository and data identified as being from a second multi-participant survey to a second study data repository.

In some cases, data collected from about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 electronic devices can be transferred from a staging data repository. In some cases, data collected from about 2 to about 10, about 10 to about 100, about 100 to about 1000, about 1000 to about 10,000, about 10,000 to about 100,000, about 100,000 to about 1,000,000, about 1,000,000 to about 10,000,000, or about 10,000,000 to about 100,000,000 electronic devices can be transferred from a staging data repository.

In some cases, data collected from about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 multi-participant surveys can be transferred from a staging data repository. In some cases, data collected from about 2 to about 10, about 10 to about 100, about 100 to about 1000, about 1000 to about 10,000, about 10,000 to about 100,000, about 100,000 to about 1,000,000, about 1,000,000 to about 10,000,000, or about 10,000,000 to about 100,000,000 multi-participant surveys can be transferred from a staging data repository.

In some cases, data collected from about, more than, less than, or at least 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 subjects, e.g., patients can be transferred from a staging data repository. In some cases, data collected from about 2 to about 10, about 10 to about 100, about 100 to about 1000, about 1000 to about 10,000, about 10,000 to about 100,000, about 100,000 to about 1,000,000, about 1,000,000 to about 10,000,000, or about 10,000,000 to about 100,000,000 subjects, e.g., patients can be transferred from a staging data repository.

In another embodiment, a computer readable medium provided herein comprises sequences of instructions, which, when executed by a computer system, cause the computer system to transfer, from the staging data repository, data identified as being from a first participant in a first multi-participant survey to a first study data repository and the data identified as being from a second participant in a second multi-participant survey to a second study data repository. In another embodiment, a computer readable medium provided herein comprises sequences of instructions, which, when executed by a computer system, cause the computer system to transfer, from a staging data repository, data identified as being from a first multi-participant survey to a first study data repository and data identified as being from a second multi-participant survey to a second study data repository.

In another embodiment, a system provided herein comprises computer readable instructions for transferring, from a staging data repository, data identified as being from a first participant in the first multi-participant survey to a first study data repository and data identified as being from a second participant in a second multi-participant survey to a second study data repository. In another embodiment, a system provided herein comprises computer readable instructions for transferring, from a staging data repository, data identified as being from a first multi-participant survey to a first study data repository and data identified as being from a second multi-participant survey to a second study data repository.

Figure 3:
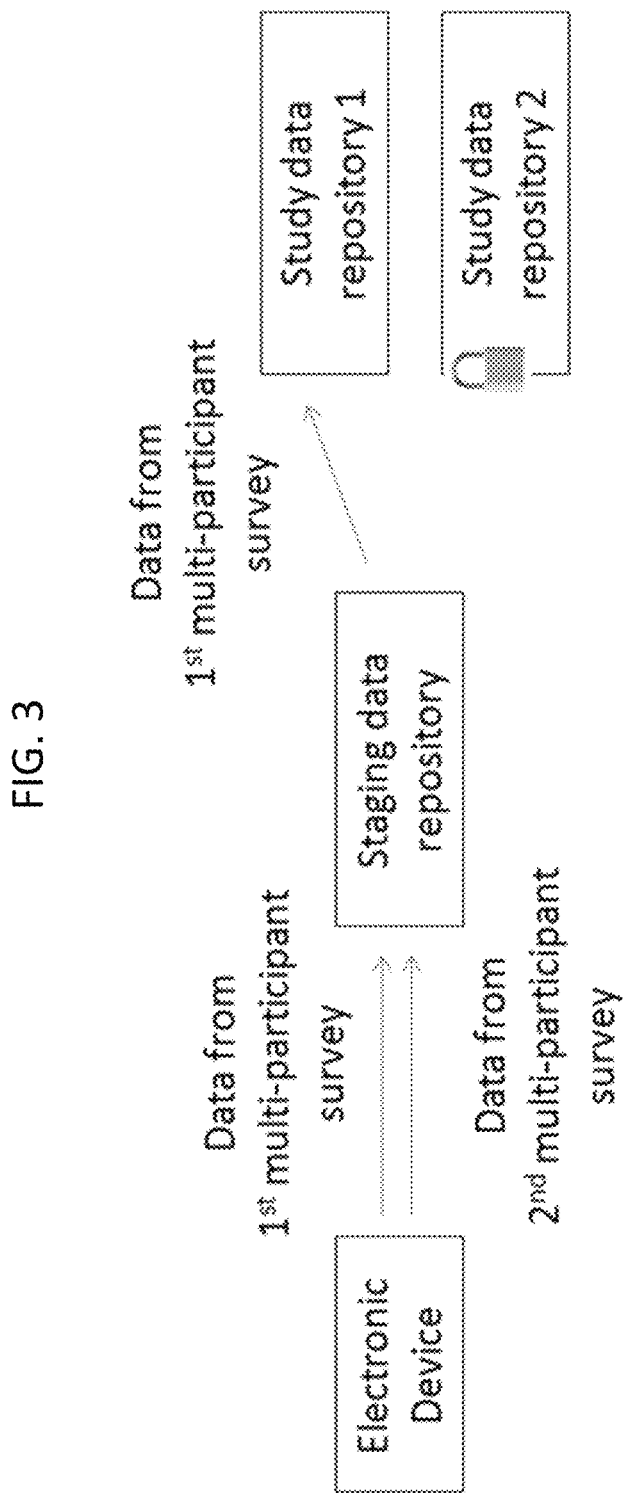
FIG. 3 illustrates locking of study data repository 2 to prevent data from entering study data repository 2.

One or more of the plurality of study data repositories can be locked. Locking a study data repository can prevent data in a staging data repository from being transferred to the locked study data repository (see e.g., FIG. 3). The number of study data repositories that can be locked can be about, at least, more than, or less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 5000, 10,000, 100,000, 1,000,000, 10,000,000, or 100,000,000 study data repositories. The number of study data repositories that can be locked can be about 2 to about 1000, about 2 to about 500, about 2 to about 100, about 2 to about 50, about 2 to about 25, about 2 to about 10, about 2 to about 5, about 10 to about 1000, about 10 to about 500, about 10 to about 100, about 10 to about 50, about 10 to about 25, or about 10 to about 15 study data repositories. The number of study data repositories that can be locked can be about 100 to about 1000, about 1000 to about 10,000, about 10,000 to about 100,000, about 100,000 to about 1,000,000, about 1,000,000 to about 10,000,000, or about 10,000,000 to about 100,000,000. In some cases, all available study data repositories are locked. In some cases, no study data repositories are locked.

In one embodiment, a method provided herein comprises locking at least one of the plurality of study data repositories. In another embodiment, a computer readable medium provided herein comprises sequences of instructions, which, when executed by a computer system, cause the computer system to lock at least one of the plurality of study data repositories. In another embodiment, a system provided herein comprises computer readable instructions for locking at least one of a plurality of study data repositories.

One or more study data repositories can be added or removed from communication with a staging data repository. The number of study data repositories that can be added or removed from communication with a staging data repository can be about, at least, more than, or less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 5000, 10,000, 100,000, 1,000,000, 10,000,000, or 100,000,000 study data repositories. The number of study data repositories that can be added or removed from communication with a staging data repository can be about 2 to about 1000, about 2 to about 500, about 2 to about 100, about 2 to about 50, about 2 to about 25, about 2 to about 10, about 2 to about 5, about 10 to about 1000, about 10 to about 500, about 10 to about 100, about 10 to about 50, about 10 to about 25, or about 10 to about 15 study data repositories. The number of study data repositories that can be added or removed from communication with a staging data repository can be about 100 to about 1000, about 1000 to about 10,000, about 10,000 to about 100,000, about 100,000 to about 1,000,000, about 1,000,000 to about 10,000,000, or about 10,000,000 to about 100,000,000.

In one embodiment, a method provided herein comprises adding or removing one or more study data repositories from communication with a staging data repository. In another embodiment, a computer readable medium provided herein comprises sequences of instructions which, when executed by a computer system, cause the computer system to add or remove one or more study data repositories from communication with a staging data repository. In another embodiment, a system provided herein comprises computer readable instructions for adding or removing at least one study data repository from communication with a staging data repository.

Figure 4:
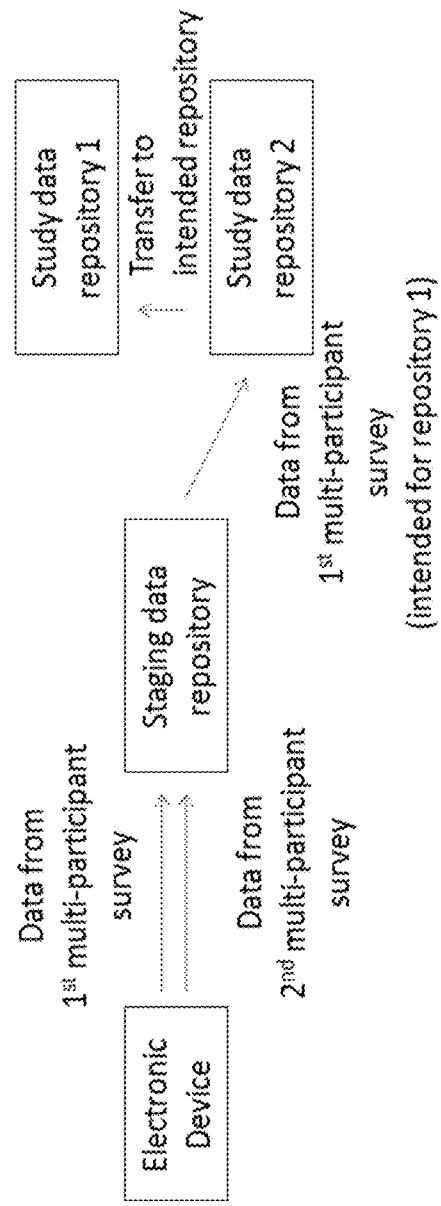
FIG. 4 illustrates transfer of data erroneously transferred to study data repository 2 to the correct study data repository 1.

In one embodiment, data intended for a first study data repository can be transferred from a staging data repository to an unintended study data repository. The data transferred to the unintended study data repository can be transferred directly from the unintended study data repository to the intended first study data repository (see e.g., FIG. 4). The data transferred to the unintended study data repository need not be transferred back to the staging data repository before transferring the data to the intended study data repository.

In one embodiment, a method provided herein comprises identifying data as being from a first participant in a first multi-participant study that is transferred from a staging data repository to the second study data repository (i.e., data that is transferred to an unintended study data repository), and transferring, from the second study data repository to a first study data repository, the data identified as being from the first participant in the first multi-participant study that was transferred from the staging data repository to the second study data repository. In another embodiment, a computer readable medium provided herein comprises sequences of instructions, which, when executed by a computer system, cause the computer system to identify data as being from a first participant in a first multi-participant study that is transferred from a staging data repository to the second study data repository (i.e., data that is transferred to an unintended study data repository), and transferring, from the second study data repository to a first study data repository, the data identified as being from the first participant in the first multi-participant study that was transferred from the staging data repository to the second study data repository. In another embodiment, a system is provided herein comprising computer readable instructions for identifying data as being from a first participant in a first multi-participant study that is transferred from a staging data repository to the second study data repository (i.e., data that is transferred to the unintended study data repository), and transferring, from the second study data repository to a first study data repository, the data identified as being from the first participant in the first multi-participant study that was transferred from the staging data repository to the second study data repository.

Computer Readable Medium and Systems

A computer readable medium can comprise instructions recorded on the computer readable medium suitable for use in an electronic device, e.g., a computer, computer network server, portable electronic device, or electronic device described herein. Computer readable media can be configured to include data or computer executable instructions for manipulating data. The computer executable instructions can include data structures, objects, programs, routines, or other program modules that can be accessed by a processing system, such as one associated with a general purpose computer capable of performing different functions or one associated with a special purpose computer capable of performing a limited number of functions. Computer executable instructions can cause a processing system to perform a particular function or group of functions and are examples of program codes for implementing steps for methods disclosed herein. A particular sequence of executable instructions can provide an example of corresponding acts that can be used to implement such steps. Computer readable media includes, e.g., a hard disk, diskette, random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), CD±R, CD±RW, DVD, DVD±RW, DVD±R, DVD-RAM, HD DVD, HD DVDR, HD DVD±RW, HD DVD±RAM, Blu-ray Disc, optical or magnetic storage medium, paper tape, punch cards, optical mark sheets or any other device that is capable of providing data or executable instructions that can be accessed by a processing system. Computer readable medium are described, e.g., in U.S. Pat. No. 7,783,072.

Computer code devices can include, e.g., scripts, dynamic link libraries (DLLs), interpretable programs, Java classes and applets, Common Object Request Broker Architecture (COBRA), or complete executable programs.

Systems provided herein can comprise one or more electronic devices that are in electronic communication. The one or more electronic devices can be connected by a wireless and/or wired connection.

In one aspect, a system for managing data from a plurality of multi-participant surveys is provided. The system can comprise an electronic device. The electronic device can comprise logic for receiving data from a first participant in a first multi-participant survey, wherein the data from the first participant are identified for analysis as being from the first participant or as being from the first multi-participant survey. The electronic device can comprise logic for receiving data from a second participant in a second multi-participant survey into the electronic device, wherein the first multi-participant survey is different from the second multi-participant survey, and wherein the data from the second participant are identified for analysis as being from the second participant or as being from the second multi-participant survey. The electronic device can comprise logic for aggregating the data from the first participant or the data from the first multi-participant survey for analysis. The electronic device can comprise logic for aggregating the data from the second participant or the data from the second multi-participant survey for analysis. The electronic device can comprise storage adapted to store the aggregated data from the first participant or the data from the first multi-participant survey and the aggregated data from the second participant or the data from the second multi-participant survey. The system can comprise a staging data repository. The staging data repository can comprise an interface for communication with said electronic device. The staging data repository can comprise logic for receiving data from said electronic device through said communication interface. The staging data repository can comprise storage adapted to receive the aggregated data from the first participant or the data from the first multi-participant survey and the aggregated data from the second participant or the data from the second multi-participant survey. The system can comprise a plurality of study data repositories. The plurality of study data repositories can comprise an interface for communication with said staging data repository. The plurality of study data repositories can comprise logic for receiving data from said staging data repository. The plurality of study data repositories can comprise logic for processing data from said staging data repository. The logic used in any component in the system can comprise electronic circuitry, computer program code, or electronic circuitry and computer program code.

Multi-Participant Survey

Data from a plurality of multi-participant surveys can be entered into an electronic device described herein. A multi-participant survey can be, e.g., a clinical trial. The clinical trial can be, e.g., a treatment trial, a prevention trial, a diagnostic trial, a screening trial, or a quality of life trial. The multi-participant survey can be a phase of a clinical trial. The phase of a clinical-trial can be, e.g., Phase 0, Phase 1, Phase 2, Phase 3, or Phase 4. Phase 0 can be an exploratory study involving very limited human exposure to a drug, with no therapeutic or diagnostic goals (for example, screening studies, microdose studies). The multi-participant survey can assess the safety and efficacy of a drug, device, or treatment. Phase 1 can be a study conducted with healthy volunteers and that emphasizes safety. The goal of a Phase 1 study can be to find out what a drug's most frequent and serious adverse events can be and to determine how the drug can be metabolized and excreted. Phase 2 can be a study that gathers preliminary data on effectiveness (e.g., whether a drug works in people who have a certain disease or condition). For example, participants receiving a drug may be compared with similar participants receiving a different treatment, e.g., an inactive substance (placebo) or a different drug. Safety can continue to be evaluated, and short-term adverse events can be studied. Phase 3 can be a study that gathers more information about safety and effectiveness by studying different populations and different dosages and by using a drug in combination with other drugs. Phase 4 can be a study occurring after FDA has approved a drug for marketing. These studies can include post-market requirement and commitment studies that can be required of, or agreed to, by a sponsor of a clinical trial. These studies can be used to gather additional information about a drug's safety, efficacy, or optimal use. The multi-participant survey can be an Expanded Access Study. The clinical trial can be sponsored by, e.g., one or more physicians, medical institutions, foundations, voluntary groups, pharmaceutical companies, National Institutes of Health (NIH), the Department of Defense (DOD), or the Department of Veteran's Affairs (VA). The clinical trial can take place, e.g., at a hospital, university, doctor's office, or community clinic.

In another embodiment, a multi-participant survey is a poll, e.g., an exit poll, e.g., a poll conducted of voters after the voters vote in a local, state, or federal election. The multi-participant survey can be an exit poll for an election in the United States or in another country. The exit poll can contain one or more questions regarding one or more candidates for president, U.S. senator, U.S. representative, governor, state senator, state representative, mayor, city council member, etc. In some cases, the poll is a poll conducted before an election (e.g., opinion poll), e.g., about, more than, less than, or at least 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 30 months, 36 months, 42 months, or 48 months before an election. The opinion poll can ask whom a potential voter plans to vote for in an election. The poll can be conducted by a private company, e.g., media organization (e.g., newspaper, television station, television broadcast company, radio station, or online newspaper or magazine). In some cases, the poll can be conducted by a political party, e.g., Republican Party, Democratic Party, Libertarian Party, Green Party, or Constitution Party. In some cases, the pool is conducted by a political action committee (PAC).

In some cases, the poll can be a poll of coaches, members of the media, or others for the purpose of ranking athletic teams, e.g., National Collegiate Athletic Association (NCAA) (Division I, II, or III), National Association of Intercollegiate Athletics (NAIA), high school (state and national level) basketball teams, football teams, volleyball teams, cross country teams, lacrosse teams, tennis teams, golf teams, gymnastics teams, wrestling teams, etc.

In another embodiment, a multi-participant survey can be a customer service survey. The customer-service survey can comprise questions relating to timeliness of service or quality of service. The service can be associated with a restaurant, lodging facility (e.g., hotel, motel, inn, lodge, or hostel), department store, electronics store, computer support, automobile repair, purchase from the Internet, or academic institution (e.g., high school, college, university, graduate school, law school, or medical school), tourist location, cruise, group vacation, home repair, spa, resort, etc.

The multi-participant survey can be a market survey. The market survey can ask questions regarding competitors, market structure, government regulations, economic trends, and/or technological advances.

The multi-participant survey can be used for advertising research. The advertising research can comprise analyzing audience levels of attention, brand linkage, motivation, entertainment, communication, flow of attention, and flow of emotion. The multi-participant survey can comprise ad tracking (e.g., periodic or continuous in-market research to monitor a brand's performance using measures such as brand awareness, brand preference, and product usage). In some cases, the multi-participant survey can comprise brand equity research (e.g., how favorably do consumers view a brand?), brand association research (e.g., what do consumers associate with a brand?), brand attribute research (e.g., what are the key traits that describe the brand?), brand name testing (e.g., what do consumers feel about the names of products?). The multi-participant survey can comprise concept testing (e.g., to test the acceptance of a concept by target consumers); "coolhunting" (e.g., to make observations and predictions in changes of new or existing culture); buyer decision process research (e.g., to determine what motivates a subject to buy and what decision-making process they use); customer satisfaction research (e.g., quantitative or qualitative studies that yield an understanding of a customer's satisfaction with a transaction); demand estimation (e.g., to determine the approximate level of demand for a product); distribution channel audits (e.g., to assess distributors' and retailer's attitudes toward a product, brand, or company); mystery consumer or mystery shopping (e.g., a subject anonymously contacts a salesperson and indicates he or she is shopping for a product; the subject can then record one or more aspects of the shopping experience); price elasticity testing (e.g., to determine how sensitive customers are to price changes); sales forecasting (e.g., to determine the expected level of sales given the level of demand, e.g., with respect to other factors, e.g., advertising expenditure, sales promotion, etc.); segmentation research (e.g., to determine demographic, psychographic, and behavioral characteristics of potential buyers); or test marketing (e.g., a small-scale product launch to test likely acceptance in a wider market).

In another embodiment, a multi-participant survey can be a product survey. The product can be, e.g., an automobile, an appliance (e.g., a refrigerator, an oven, a microwave, a stove, a dishwasher, a washing machine, a dryer), toy, clothing, shoes, food, cleaning product, utensil, carpet, electronic device (e.g., computer, television, audio system), yard equipment (e.g., mower), or athletic event. The product survey can inquire about a consumer's opinions regarding a product, a consumer's opinion of the brand of the product, or a consumer's awareness of a product, or how a consumer compares a product to a competitor's product. The product survey can assess effects of marketing efforts. A product survey can assess a consumer's level of satisfaction with a product.

In another embodiment, a multi-participant survey can be a public opinion survey or poll. The public opinion survey or poll can comprise questions regarding the economy, public health, health care, consumer confidence, public policy, opinions toward one or more officeseekers, voting behavior, attitudes toward economic, social, or political priorities, attitudes toward economic development, issues relevant to a particular geographic area (e.g., state, county, city, or neighborhood), attitudes toward ballot initiatives, attitudes towards foreign affairs, attitudes towards the military, attitudes towards conflicts (e.g., battles, wars), attitudes towards education (primary, secondary, post-secondary, graduate), political events, work, family life, the press, the media, economic conditions, ethical issues, scientific research, underage drinking, charitable giving, federal elected officials, state elected officials, quality of life, quality of life in a specific geographic area (e.g., state, county, city, or neighborhood), attitudes towards political candidates and election issues, ethical and public policy implications of scientific discovery, attitudes on crime, lotteries, race relations, underage drinking, charitable giving, health care privacy, privacy, drug abuse, environment, immigration; statewide referenda, social issues, performance of federal and state elected officials, environment, education, fiscal policy, local, state, or federal government response to a national disaster, social values held by individuals, religion, role of government, social inequality, attitudes toward democratic values and behaviors; athletics, athletic teams, or lifestyle (e.g., frequency of exercise, alcohol consumption). The public opinion survey can be conducted by a private company, e.g., media organization (e.g., newspaper, television station, television broadcast company, radio station, or online newspaper or magazine).

In another embodiment, a multi-participant survey can be a survey of witnesses of an event. The event can be, e.g., an alleged crime. The alleged crime can be, e.g., robbery, burglary, assault, battery, shooting, murder, sexual assault, or rape. The event can be, e.g., an accident. The accident can be, e.g., a traffic accident, an injury, a fall, a chemical spill, a hazardous waste spill, a radiation spill, an explosion, or a workplace accident. The event can be a natural disaster, e.g., tornado, hurricane, typhoon, cyclone, tsunami, blizzard, volcanic eruption, landslide, mudslide, drought, flood, severe thunderstorm, insect infestation, or earthquake. The event can be an attack, e.g., a terrorist attack, a biological weapon attack, a chemical weapon attack, a nuclear attack, or an invasion. In another embodiment, a multi-participant survey comprises a police line-up.

In another embodiment, a first multi-participant survey and a second multi-participant survey can be concurrent. In some embodiments, at least part of the first multi-participant survey occurs while at least part of the second multi-participant survey occurs. In one embodiment, a first multi-participant survey ends before a second multi-participant survey begins. In some cases, a plurality of multi-participant surveys is concurrent.

Data from a plurality of multi-participant surveys can be entered into an electronic device. For example, data from about, at least, less than, or more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 multi-participant surveys can be entered into an electronic device. Data from 2 to 3, 2 to 4, 2 to 5, 2 to 6, 2 to 7, 2 to 8, 2 to 9, 2 to 10, about 10 to about 20, about 10 to about 50, about 50 to about 100, about 100 to about 1000, about 1000 to about 5000, about 5000 to about 10,000, about 10,000 to about 50,000, about 50,000 to about 100,000, about 100,000 to about 500,000, about 500,000 to about 1,000,000, about 1,000,000 to about 10,000,000, about 10,000,000 to about 50,000,000, or about 50,000,000 to about 100,000,000 multi-participant surveys can be entered into an electronic device.

In one embodiment, data from more than one multi-participant survey of the same type can be entered into an electronic device. For example, data from more than one clinical trial can be entered into an electronic device. In another embodiment, data from more than one multi-participant survey of different types can be entered into an electronic device. For example, data from a clinical trial and data from a public opinion survey can be entered onto an electronic device.

A plurality of multi-participant surveys can comprise surveys conducted by the same individual or group or surveys conducted by different individuals or groups.

Participants

The first participant in a first multi-participant survey and the second participant in a second multi-participant can be the same person. For example, the same person can participate in two different multi-participant surveys, and data from the same person can be entered into an electronic device. In one embodiment, the first participant and the second participant are different people. For example, the data from the first participant participating in a first multi-participant survey can be entered into an electronic device, and data from the second participant participating in the first multi-participant survey can be entered into the device. In one embodiment, data from the first participant participating in a first multi-participant survey can be entered into an electronic device, and data from the second participant participating in a second multi-participant survey can be entered into the device, wherein the first participant and second participant are different people and the first multi-participant survey and the second multi-participant survey are different.

Data from a plurality of participants in one or more multi-participant surveys can be entered into an electronic device. The plurality of participants can be about, at least, less than, or more than 5, 10, 25, 50, 75, 100, 150, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, or 100,000,000 participants in one or more multi-participant surveys. The plurality of participants can be about 100 to about 1000, about 1000 to about 5000, about 5000 to about 10,000, about 10,000 to about 50,000, about 50,000 to about 100,000, about 100,000 to about 500,000, about 500,000 to about 1,000,000, about 1,000,000 to about 10,000,000, about 10,000,000 to about 50,000,000, or about 50,000,000 to about 100,000,000 participants in one or more multi-participant surveys.

A first and/or second participant can enter data into an electronic device. In some embodiments, one or more third parties enter data from the first and/or second participant into an electronic device. In one embodiment, the one or more third parties are a relative or healthcare provider. A relative can be, e.g., spouse (husband or wife), sister, brother, aunt, uncle, grandfather, grandmother, child, or cousin. Healthcare providers are described herein.

In one embodiment, a participant is male or a female. In another embodiment, a participant is a newborn, an infant, a child, a teenager, a young adult, an adult, or an elderly person. In another embodiment, a participant can be about, at least, more than, or less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. In some cases, the age of the participants is about 1 day to about 1 year old, about 1 year old to about 4 years old, about 5 years old to about 10 years old, about 10 years old to about 12 years old, about 13 years old to about 19 years old, about 20 years old to about 29 years old, about 30 years old to about 39 years old, about 40 years old to about 49 years old, about 50 years old to about 59 years old, about 60 years old to about 69 years old, about 70 years old to about 80 years old, about 80 years old to about 90 years old, about 90 years old to about 100 years old, about 100 years old to about 110 years old, or about 110 years old to about 120 years old. In another embodiment, a participant is enrolled in a clinical trial. In another embodiment, a participant is pregnant or is suspected of being pregnant (e.g., pregnant with a single fetus, twins, triplets, etc.). In another embodiment, a participant can have a condition, e.g., cancer, autoimmune disease, neurological disorder, or diabetes. In another embodiment, a participant can have an infectious disease, e.g., a bacterial infection, fungal infection, or viral infection, e.g., influenza or AIDS.

Data

Data that can be entered into an electronic device provided herein can take a variety of forms. Data entered into an electronic device can be used for a variety of purposes.

The data can be clinical trial data. Clinical trial data can include data gathered for the principle purpose of a clinical trial. For example, clinical trial data can include pain levels experienced by subjects in a pain medication clinical trial or craving levels in an anti-smoking medication clinical trial. Clinical trial data entered into a device can include, e.g., gender of a subject, height, weight, body fat percentage, body fat index, hair color, Body Mass Index (BMI), hours of sleep per day, sleep quality index score, bowel movement schedule, pain index score, pain scale score, pain threshold test result, hearing test result, optometry exam result, appetite level, hunger scale score, number of calories consumed per day, volume of liquid consumed per day, thirst scale score, libido scale score, erection frequency, energy level, activity level, exercise level, activity type, activity schedule, well-being, nausea frequency, psychological stress level, depression level score, intelligence quotient test result, mental skill test result, exercise test result, fatigue level, disease severity, PSA level, cholesterol level, blood pressure, systolic blood pressure, diastolic blood pressure, cardiac stress test result, blood glucose level, heart rate, spirometry test result, lung volume measurement, lung diffusion capacity, $VO_2$ max, oximeter reading, biomarker level, presence or absence of a biomarker, biopsy result, time spent in sedentary activity per day, urination frequency, urination amount, frequency of social contacts, duration of social contacts, the time of the year, and the day of the week. The clinical trial data can be self-reports of clinical trial data including subjective reports, such as pain reduction, objective symptom reporting, such as bowel movement or asthmatic episode or cognitive measures, such as arithmetic tasks or reaction time. An electronic device can be configured to synchronize with any portable physiological measurement device to gather data from, or communicate with, the physiological device. Data can be derived from Phase 0, Phase 1, Phase 2, Phase 3, or Phase 4 of a clinical trial.

The clinical trial results can be clinical tests comprising tests of tissues and/or bodily fluids comprising blood tests, fatty acid tests, urine tests, plasma tests, enzyme tests, pregnancy tests, DNA tests, or cytogenetics tests, among others.

In one embodiment, an electronic device can be used to track compliance information for a plurality of multi-participant studies, e.g., clinical trials. For example, historical protocol data can be entered into an electronic device. Historical protocol data can include data specifying a research protocol of an earlier clinical trial. Examples of historical protocol data can include questions posed to a subject, frequency of prompting of a subject during various times of a day or week, time allowed for subjects to respond to one or more questions, requirements of subject behavior, and conditions mandating removal of a subject from specific analyses or from participation in a clinical trial. Methods of detecting, predicting, and enhancing subject compliance, e.g., subject compliance with a research protocol, are described, e.g., in U.S. Pat. Nos. 6,879,970, 7,415,447, 7,873,589, 8,065,180, and 8,145,519, which are herein incorporated by reference in their entireties. Compliance can include complete compliance, good compliance, non-compliance, or minor non-compliance.

In some cases, data entered into an electronic device can be used to determine or predict fraud with a research protocol in a clinical trial. Methods and devices for detecting or predicting fraud are described in U.S. Pat. Nos. 6,879,970, 7,415,447, and 7,873,589, which are herein incorporated by reference in their entireties. Data determined or predicted to be fraudulent can be excluded from a data set. In some cases, data determined to be fraudulent can be removed from an electronic device, a staging data repository, or a study data repository. In some cases, the fraud is committed by a subject in a multi-participant survey (e.g., clinical trial). In some cases, the fraud is committed by a sponsor of a multi-participant survey (e.g., clinical trial).

In some cases, data entered into an electronic device can be evaluated to determine or predict the validity of the data (e.g., whether entered data is within an acceptable range). Data determined or predicted to be invalid can be excluded from a data set. In some cases, data determined or predicted to be invalid can be removed from an electronic device, a staging data repository, and/or a study data repository. Methods and devices for detecting or predicting invalid data are described, e.g., in U.S. Pat. Nos. 6,879,970, 7,415,447, 7,873,589, 8,065,180, and 8,145,519, which are herein incorporated by reference in their entireties.

Compliance data can be entered into an electronic device. Compliance data can be data that relates to the circumstances under which clinical trial data are collected or other data pertaining to characteristics of clinical trial data. Examples of compliance data include timeliness, consistency with other collected data, proximity of the data to an expected data range, and completeness of the data.

An electronic device can track aspects of its use, which can result in a comprehensive record of subject compliance with a research protocol. Clinical trial staff can collect data regarding subject compliance by tracking a variety of different components of compliance. Clinical trial staff can check compliance against empirically derived algorithms and decision rules of compliance. These empirically derived algorithms and decision rules allow the disclosed invention to examine the data for nonintuitive and complex combinations of predictors to proactively determine whether the observed pattern of interaction with the portable electronic device suggests noncompliance.

An electronic device can conduct ongoing compliance checks and provide a subject feedback about his or her performance. For example, logical psychometric or other inconsistencies can be determined by an electronic device. Actions of an electronic device can be processed according to decision rules. An electronic device can vary its behavior based on the subject's behavior. For example, prompt frequency can be delayed or increased, or louder prompts can be provided. Vibration or visual alerts can be generated.

Compliance checks can be performed on a server and feedback can be given to a subject by clinical trial staff; the feedback can be face-to-face or remote.

When the multi-participant survey is a clinical trial, data can be used to track and enhance subject compliance with protocol requirements and provide evaluability data related to subject performance in the clinical trial. For example, an empirically derived set of algorithms and decision rules can be used to predict, track and enhance subject compliance with research protocols in a clinical trial. Algorithms and decision rules can be used for analysis of different types of subject noncompliance with research protocols.

Algorithms for detecting or predicting subject compliance, fraud, or data invalidity, and methods for developing algorithms for detecting or predicting subject compliance, fraud, or data invalidity, are described in U.S. Pat. Nos. 6,879,970, 7,415,447, 7,873,589, 8,065,180, and 8,145,519, which are herein incorporated by reference in their entireties.

In some cases, the data provided herein can be used to predict the reliability of endpoints in supporting one or more medical labeling claims. Methods, systems, and devices for predicting the reliability of endpoints in supporting one or more medical labeling claims are described, e.g., in U.S. Patent Application Publication No. 2100023346, which is herein incorporated by reference in its entirety.

Healthcare Provider

In some embodiments, one or more healthcare providers enter data into an electronic device or provide an electronic device to a subject. A healthcare provider can be, e.g., a nurse, a physician (e.g., general practitioner or specialist) a physician assistant, a surgeon, a psychiatrist, a psychologist, clinical psychologist, clinical social worker, mental health nurse practitioner, marriage or family therapist, obstetrician, obstetrical nurse, midwife, nurse practitioner, geriatrician, geriatric nurse, geriatric aide, surgical practitioner, anesthesiologist, nurse anesthetist, surgical nurse, operating department practitioner, anesthetic technician, surgical technologist, physiotherapist, orthotist, prosthetist, recreational therapist, dental hygienist, dentist, podiatrist, pedorthist, chiropractor, a medical technician, a pharmacist, dietitian, therapist, clinical officer, phlebotomist, physical therapist, social worker, respiratory therapist, occupational therapist, audiologist, speech pathologist, optometrist, emergency medical technician, paramedic, medical laboratory technician, radiography, medical prosthetic technician, epidemiologist, or health inspector.

A healthcare provider can enter data into an electronic device for a first clinical trial, and a subject can enter data into the electronic device for a second clinical trial. A healthcare provider can enter data into an electronic device for a first clinical trial and a second clinical trial. In some embodiments, a healthcare provider does not enter data into an electronic device that is configured to accept data from a plurality of multi-participant studies. Healthcare providers can enter data in an electronic device for a plurality of multi-participant studies.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLE

Example 1

A first subject enrolls in a first clinical trial for a first pharmaceutical composition. The first subject visits a clinic and is provided doses of the first pharmaceutical composition. The first subject is also provided a portable electronic device by a healthcare provider for recording data regarding the first subject's physiological responses to the pharmaceutical composition. The portable electronic device is configured to accept data entered by the first subject regarding the first clinical trial. The portable electronic device is also configured to accept data related to a second clinical trial for a second pharmaceutical composition. The first clinical trial lasts for nine months. The first subject enters data regarding the first clinical trial into the portable electronic device. The first subject returns the portable electronic device to the healthcare provider at the end of the first clinical trial. The healthcare provider then provides the electronic device to a second subject enrolled in the second clinical trial. The second subject enters data related to the second clinical trial into the portable electronic device. At the end of the second clinical trial, the second subject returns the portable electronic device to the healthcare provider.

The electronic device communicates the data from the first subject in the first clinical trial to a staging data repository at the end of the first clinical trial. The electronic device also communicates the data from the second subject in the second clinical trial to the staging data repository at the end of the second clinical trial. The data from the first clinical trial is transferred to a first study data repository and the data from the second clinical trial is transferred to a second study data repository.

Example 2

A polling company recruits five thousand volunteers in a "swing state" to offer their opinions regarding federal and state elections in November of an election year. The company distributes portable electronic devices to the five thousand volunteers in January of the election year. The polling company sends two types of questionnaires to the volunteers at random times and/or before or after certain events. One type of questionnaire contains questions concerning federal elections; the other type of questionnaire contains questions concerning state elections. Responses to federal election questionnaires are identified electronically as being related to federal elections; responses to state election questionnaires are identified electronically as being related to state elections. Responses are entered by a touch screen. An event can include a debate, caucus, primary election, speech, convention, scandal, major world event, natural disaster, withdrawal of a candidate, etc. Volunteers must respond to each questionnaire within a specified time window after receiving the questionnaire; if the volunteer does not respond before the time window closes, the volunteers cannot enter responses for that questionnaire into the electronic device.

Data entered into the portable electronic devices are immediately transmitted to a staging data repository once the time window for responding to a questionnaire closes. Data concerning state election questionnaires is then transmitted from the staging data repository to the state election study data repository. Data concerning federal election questionnaires is transmitted from the staging data repository to a federal election study data repository. Local election study data repositories in electronic communication with the staging data repository are locked.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   a) receiving, by an electronic device, first data from a first participant in a first multi-participant survey or study, wherein the first data are identified for analysis as being from the first participant or as being from the first multi-participant survey or study;

b) receiving, by the electronic device, second data from a second participant in a second multi-participant survey or study, wherein the first multi-participant survey or study is different from the second multi-participant survey or study, and wherein the second data are identified for analysis as being from the second participant or as being from the second multi-participant survey or study;

c) transferring a first data structure based at least on the first data to a first study data repository;

d) locking the first study data repository;

e) preventing, based at least on a determination that the first study data repository is locked, a data structure from being transferred to the first study data repository; and f) after d), transferring the second data structure to a second study data repository.

2. The method of claim 1, wherein the electronic device is a portable electronic device.

3. The method of claim 1, further comprising recording the first data and the second data on the electronic device.

4. The method of claim 1, wherein the first multi-participant survey or study and the second multi-participant survey or study are concurrent.

5. The method of claim 1, wherein the first multi-participant survey or study ends before the second multi-participant survey or study begins.

6. The method of claim 1, wherein the first multi-participant survey or study or the first multi-participant survey or study is a clinical trial.

7. The method of claim 1, wherein the electronic device is located at a site.

8. The method of claim 7, wherein the site is a hospital, medical clinic, or laboratory.

9. The method of claim 1, wherein the electronic device is connected to an Internet.

10. A non-transitory computer readable medium having stored thereon sequences of instructions, which, when executed by a computer system, cause the computer system to perform:

a) receiving, by an electronic device, first data from a first participant in a first multi-participant survey or study, wherein the first data are identified for analysis as being from the first participant or as being from the first multi-participant survey or study;

b) receiving, by the electronic device, second data from a second participant in a second multi-participant survey or study, wherein the first multi-participant survey or study is different from the second multi-participant survey or study, and wherein the second data are identified for analysis as being from the second participant or as being from the second multi-participant survey or study;

c) transferring a first data structure based at least on the first data to a first study data repository;

d) locking the first study data repository;

e) preventing, based at least on a determination that the first study data repository is locked, a data structure from being transferred to the first study data repository; and f) after d), transferring the second data structure to a second study data repository.

11. The non-transitory computer readable medium of claim 10, wherein the electronic device is a portable electronic device.

12. The non-transitory computer readable medium of claim 10, wherein the electronic device is connected to an Internet.

13. The non-transitory computer readable medium of claim 10, wherein the first multi-participant survey or study and the second multi-participant survey or study are concurrent.

14. The non-transitory computer readable medium of claim 10, wherein the first multi-participant survey or study ends before the second multi-participant survey or study begins.

15. The non-transitory computer readable medium of claim 10, wherein the first multi-participant survey or study or the first multi-participant survey or study is a clinical trial.

16. The non-transitory computer readable medium of claim 10, wherein the electronic device is located at a site.

17. The non-transitory computer readable medium of claim 16, wherein the site is a hospital, medical clinic, or laboratory.

18. A system comprising one or more computer processors and a non-transitory computer readable medium having stored thereon sequences of instructions for:

a) receiving, by an electronic device, first data from a first participant in a first multi-participant survey or study, wherein the first data are identified for analysis as being from the first participant or as being from the first multi-participant survey or study;

b) receiving, by the electronic device, second data from a second participant in a second multi-participant survey or study, wherein the first multi-participant survey or study is different from the second multi-participant survey or study, and wherein the second data are identified for analysis as being from the second participant or as being from the second multi-participant survey or study;

c) transferring a first data structure based at least on the first data to a first study data repository;

d) locking the first study data repository;

e) preventing, based at least on a determination that the first study data repository is locked, a data structure from being transferred to the first study data repository; and f) after d), transferring the second data structure to a second study data repository.

19. The system of claim 18, wherein the electronic device is a portable electronic device.

20. The system of claim 18, wherein the electronic device is connected to an Internet.

21. The system of claim 18, wherein the first multi-participant survey or study and the second multi-participant survey or study are concurrent.

22. The system of claim 18, wherein the first multi-participant survey or study ends before the second multi-participant survey or study begins.

23. The system of claim 18, wherein the first multi-participant survey or study or the second multiple-participant survey or study is a clinical trial.

24. The system of claim 18, wherein the electronic device is located at a site.

25. The system of claim 24, wherein the site is a hospital, medical clinic, or laboratory.

26. The method of claim 1, further comprising transmitting the first data structure to a staging data repository and transmitting the second data structure to the staging data repository.

27. The method of claim 26, wherein the transferring the first data structure to the first study data repository comprises, by one or more servers, transferring the first data structure from the staging data repository, and the transferring, by the one or more servers, the second data structure to the second study data repository comprises transferring the second data structure from the staging data repository.

28. The non-transitory computer readable medium of claim 10, wherein the sequences of instructions, which, when executed by the computer system, cause the computer system to perform: transmitting the first data structure to a staging data repository and transmitting the second data structure to the staging data repository.

29. The non-transitory computer readable medium of claim 28, wherein the transferring the first data structure to the first study data repository comprises transferring, by one or more servers, the first data structure from the staging data repository, and the transferring the second data structure to the second study data repository comprises transferring, by one or more servers, the second data structure from the staging data repository.

30. The system of claim 18, wherein the non-transitory computer readable medium further comprises sequences of instructions for transmitting the first data structure to a staging data repository and transmitting the second data structure to the staging data repository.

31. The system of claim 30, wherein the transferring the first data structure to the first study data repository comprises transferring, by one or more servers, the first data structure from the staging data repository, and the transferring the second data structure to the second study data repository comprises transferring, by the one or more servers, the second data structure from the staging data repository.

* * * * *